(12) United States Patent
Glazer et al.

(10) Patent No.: US 9,290,528 B1
(45) Date of Patent: Mar. 22, 2016

(54) LIGHT-ACTIVATED COMPOUNDS

(71) Applicant: University of Kentucky Research Foundation, Lexington, KY (US)

(72) Inventors: Edith C. Glazer, Lexington, KY (US); David K. Heidary, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/217,307

(22) Filed: Mar. 17, 2014

Related U.S. Application Data

(60) Provisional application No. 61/799,678, filed on Mar. 15, 2013.

(51) Int. Cl.
*A61K 31/555* (2006.01)
*C07F 15/00* (2006.01)

(52) U.S. Cl.
CPC .................................. *C07F 15/0053* (2013.01)

(58) Field of Classification Search
USPC .................................. 514/185, 184; 546/10, 2
See application file for complete search history.

(56) References Cited

U.S. PATENT DOCUMENTS

| | | | |
|---|---|---|---|
| 5,608,059 A | 3/1997 | Wear et al. | |
| 5,714,089 A | 2/1998 | Bard et al. | |
| 6,979,681 B2 | 12/2005 | Morris et al. | |
| 8,063,216 B2 | 11/2011 | Etchenique et al. | |
| 2005/0181443 A1 | 8/2005 | Sun et al. | |
| 2006/0111335 A1 | 5/2006 | Morrison et al. | |
| 2007/0082881 A1 | 4/2007 | MacDonnell et al. | |
| 2007/0161069 A1 | 7/2007 | Rose et al. | |
| 2008/0176940 A1 | 7/2008 | Etchenique et al. | |
| 2012/0116287 A1 | 5/2012 | Etchenique et al. | |

OTHER PUBLICATIONS

Wachter, E. et al.: Light-activated ruthenium complexes photobind DNA and are cytotoxic in the photodynamic therapy window. Chem. Commun., vol. 48, pp. 9649-9651, 2012.*
Yu, H-J. et al.: Synthesis, visible light photocleavage, antiproliferative and cellular uptake properties of ruthenium complex. Eur. J. Medicin. Chem., vol. 55, pp. 14154, 2012.*
Sun, Y. et al.: Efficient DNA photocleavage by [Ru(bpy)2(dppn)]2+ with visible light. Chem. Commun., vol. 46, pp. 2426-2428, 2010.*
Monro, S. et al.: Photobiological activity of Ru(II) based on (pyren-1-yl)ethynyl derivatives of 1,10-phenanthroline. Inorganic Chem., vol. 49, pp. 2889-2900, 2010.*
Juris, et al., Ru(II) Polypyridine Complexes: Photopi3ysics, Photochemwt'ry, Eleci?Rochemistry, and Chemilumine Scence; Coordination Chemistry Reviews, 84 (1988) 85-277.

\* cited by examiner

*Primary Examiner* — Charanjit Aulakh
(74) *Attorney, Agent, or Firm* — Stites & Harbison PLLC; Mandy Wilson Decker

(57) ABSTRACT

The presently-disclosed subject matter includes light-activated ruthenium compounds. In some embodiments the compounds release one or more ligands when exposed to light, and in specific embodiments the light includes a wavelength of about 500 nm to about 1000 nm. The present compounds can also comprise an overall charge, wherein the overall charge can be a positive overall charge or a negative overall charge. Further still, embodiments include methods of treating cancer in a subject by administering a compound and then exposing a site of the subject to light.

34 Claims, 14 Drawing Sheets

LIGHT-ACTIVATED COMPOUNDS

RELATED APPLICATIONS

This applications claims priority from U.S. Provisional Application Ser. No. 61/799,678, filed Mar. 15, 2013, the entire disclosure of which is incorporated herein by this reference.

TECHNICAL FIELD

The presently-disclosed subject matter relates to light-activated compounds. In particular, presently-disclosed subject matter relates to light-activated ruthenium compounds as well as methods for using the same.

INTRODUCTION

Photoactivation is an elegant method to convert non-toxic prodrugs to active cytotoxic species in a spatially and temporally controlled manner. Photoactivation provides a mechanism to discriminate between malignant tissues of tumors and the surrounding healthy tissues, potentially reducing the dose-limiting side effects incurred with standard chemotherapies. Photodynamic therapy (PDT) uses this light-targeted approach, and has been successfully applied in the treatment of various cancers, notably of the lung, esophagus, and skin.

PDT commonly requires a photosensitizer such as a porphyrin to generate singlet oxygen ($^1O_2$), which is the actual toxic moiety. However, this requirement for oxygen has limited the utility of PDT, due to the hypoxic nature of many tumors. Known porphyrin-type organic photosensitizers used in PDT also have other poor chemical characteristics, and suffer from photobleaching, poor solubility, and retention in tissues, causing protracted photosensitivity.

In light of these drawbacks, several groups are investigating photoactive metal compounds (complexes) as alternative PDT agents. For instance, ruthenium polypyridyl compounds have tunable absorption properties, and can induce $^1O_2$-mediated DNA photocleavage when exposed to UV to visible light. Some ruthenium agents also can act via oxygen-independent mechanisms, allowing for activity in hypoxic tissues. However, unlike organic PDT sensitizers, known metal compounds are not activated, and therefore are not cytotoxic, within the "therapeutic window" for PDT, which includes red and near infrared (IR) light from 600-1100 nm.

Hence, there remains a need for improved PDT agents, and specifically compounds that are thermally inert and that can be triggered by low energy, visible light to generate toxic species for use as, for example, chemotherapeutics. There are remains a need for agents that are easy to synthesize, have a flexible design that can be modified without unduly compromising efficacy, and retain activity in the presence of biological reducing agents, such as glutathione. Further still, there remains a need for agents having structural motifs that are distinct from those of known agents (e.g., square planar platinum compounds) so that they may retain efficacy in subjects that have otherwise developed resistance to known drugs, such as cisplatin and its analogues.

BRIEF DESCRIPTION OF THE DRAWINGS

(FIG. 14C) 10, dark; (FIG. 14D) 10, irradiated. TMRE was used to quantify membrane potential; values are relative to a no-compound control value of 100.

DESCRIPTION OF EXEMPLARY EMBODIMENTS

Figure 1:
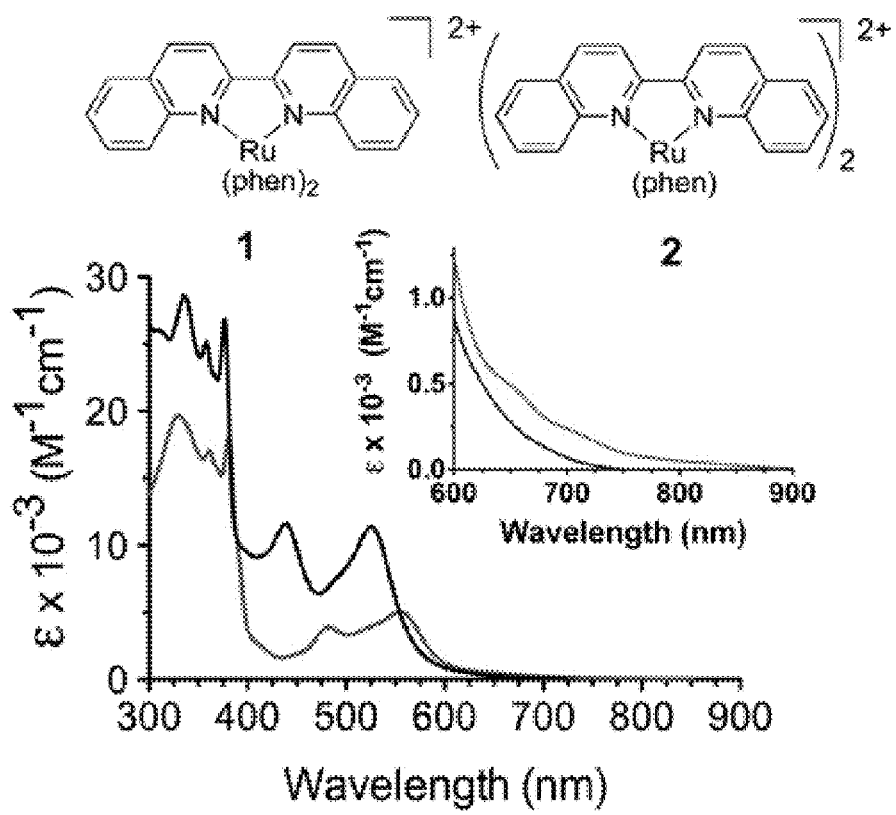
FIG. 1 includes structures showing Ru(II) complexes, and further includes charts showing the UV/Vis absorption spectra of 1 (black) and 2 (gray), where the inset shows the absorption in a region of the PDT window (600 nm-900 nm).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes light-activated metal compounds, and in particular, certain embodiments include ruthenium (Ru) compounds. In some embodiments of ruthenium compounds comprise a ruthenium metal core and one or more ligands, wherein one or more ligands are released from the ruthenium metal center when the compound is exposed to light. As used herein, the terms "compound," "complex," and the like are used interchangeably to refer to embodiments of light-activated metal substances.

More specifically, the presently-disclosed subject matter includes compounds having structures represented by the following formula:

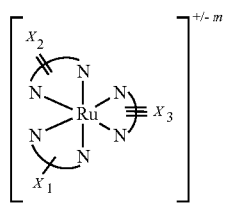

wherein $X_1$, $X_2$, and $X_3$, the same or different from one another, are selected from bidentate nitrogen heterocycles, metallocycles, or a combination thereof, and are optionally substituted with one or more of alkyl, aryl, amine, C(O), C(O)R, S, S(R), O, O(R), and P, wherein R is selected from H, OH, alkyl, and aryl, and m is −6 to +6.

As used herein, the term "substituted" is contemplated to refer to compounds that have been modified with any and all permissible substituents. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate compounds. For example, in some embodiments the compounds that comprise polypyridyl ligands that have been substituted with alkyl substituents and/or any other permissible substituents described herein. In certain embodiments the present compounds are substituted with a substituent that can induced strain in the compounds. This disclosure is not intended to be limited in any manner by the permissible substituents of the present compounds.

Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$", or the like, are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

In this regard, the term "heterocycle," as used herein refers to single and multi-cyclic aromatic or non-aromatic ring systems in which at least one of the ring members is other than carbon. Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by a formula —C(O)H. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

Reference to any of the compounds described here also includes reference to any pharmaceutically acceptable derivative thereof, regardless of whether this is expressly stated for each compound. The term "derivative" is used herein to refer to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound. The term "pharmaceutically acceptable" describes a material that is not biologically or otherwise undesirable, i.e., without causing an unacceptable level of undesirable biological effects or interacting in a deleterious manner.

In some embodiments at least one of $X_1$, $X_2$, and $X_3$ (i.e., ligands) are released when the compound is exposed to light. In this regard, in some embodiments the compounds comprise at least one ligand that is inherently strain-inducing and/or a ligand that includes a strain-inducing group (substituent). The term "strain-inducing group" generally refers to the general characteristic of a group that can create a steric clash in a compound. In specific embodiments "strain-inducing" refers to the characteristic of a compound having bond lengths and/or bond angles that deviate by 5% or more relative to the ideal bond lengths and/or bond angles determined by VSEPR theory. Such determinations can be made by analyzing the crystal structure of a compound, for example.

Thus, in some embodiments at least one of $X_1$, $X_2$, and $X_3$ can be a strain-inducing ligand that produces a steric clash in the compound, which can facilitate release of the ligands upon being exposed to certain light. In some instances the term strain inducing is used to refer to a group or substituent that gives rise to strain-inducing properties. For example, a ligand can be substituted with one or more strain-inducing groups that impart a strain-inducing characteristic to the ligand. In specific embodiments the strain-inducing group is located in a ligand at a position ortho to the chelating nitrogen of a bidentate nitrogen heterocycle.

Some exemplary ligands are represented by the formula:

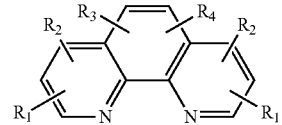

wherein each $R_1$ is independently selected from H, amine, amide, alkyl, aryl, $SR_4$, $PR_4$, O, $OR_4$, halogen, or $SO_3H$, $R_4$ being H, alkyl, or aryl, or wherein $R_1$ and $R_3$ taken together with the carbon atoms to which they are bonded, form a substituted or unsubstituted ring containing about 4-6 ring carbon atoms that optionally include one or more N, each $R_2$ is H, amine, amide, alkyl, aryl, $SR_4$, $PR_4$, O, $OR_4$, halogen, or $SO_3H$, each $R_3$ is independently selected from H, amine, amide, alkyl, aryl, $SR_4$, $PR_4$, O, $OR_4$, halogen, or $SO_3H$, or wherein $R_3$ and $R_4$ taken together with the carbon atoms to which they are bonded, form a substituted or unsubstituted ring containing about 4-6 ring carbon atoms that optionally include one or more N, and each $R_4$ is H, amine, amide, alkyl, aryl, $SR_4$, $PR_4$, O, $OR_4$, halogen, or $SO_3H$.

In some embodiments exemplary ligands are represented by the formula:

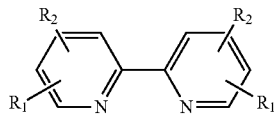

wherein each $R_1$ is independently selected from H, amine, amide, alkyl, aryl, $SR_4$, $PR_4$, O, $OR_4$, halogen, or $SO_3H$, $R_4$ being H, alkyl, or aryl, or wherein $R_1$ and $R_3$ taken together with the carbon atoms to which they are bonded, form a substituted or unsubstituted ring containing about 4-6 ring carbon atoms that optionally include one or more N, and each $R_2$ is H, amine, amide, alkyl, aryl, $SR_4$, $PR_4$, O, $OR_4$, halogen, or $SO_3H$.

In other embodiments exemplary ligands are represented by the formula:

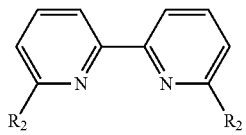

wherein $R_1$ and $R_2$, the same or different from one another, are any group other than H. In some embodiments the strain-inducing group (e.g., $R_1$ and $R_2$) is an alkyl, such as a methyl group. Other examples of strain-inducing groups include, but are not limited to, cycloalkyl, phenyl, aryl, and heteroatom (e.g., N, O, S, P, Cl, Br, I, etc.) substituents. The ligands can be selected from the group consisting of, but are not limited to, 2,2'-bipyridyl, dipyrido[3,2-f:2',3'-h]-quinoxaline, 1,10-phenanthroline, hydroxyquinoline, and the like.

A non-limiting list of exemplary ligands, both strain-inducing and not, that can be incorporated in compounds of the presently-disclosed subject matter also include those represented by the following structures:

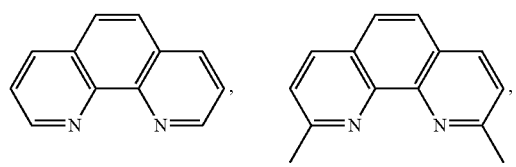

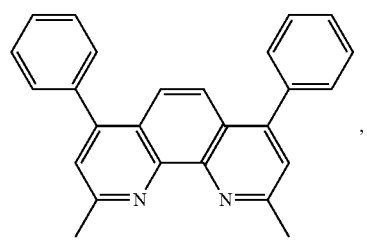

-continued

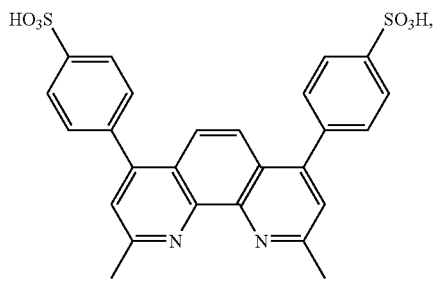

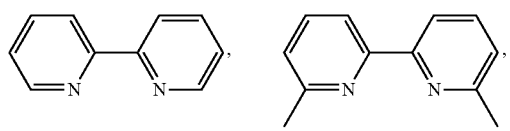

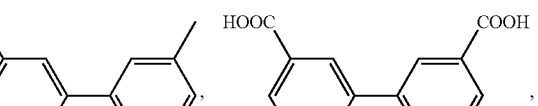

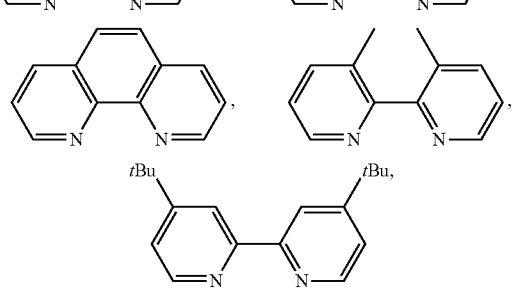

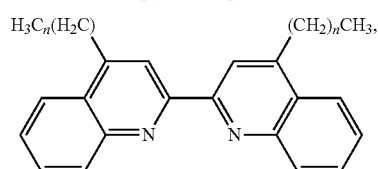

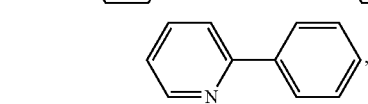

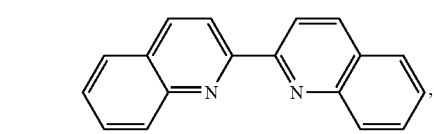

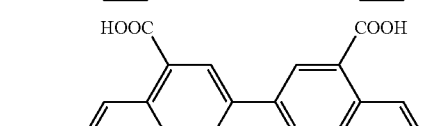

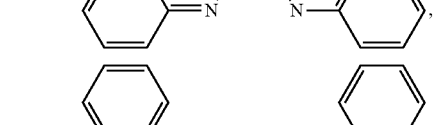

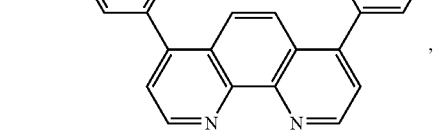

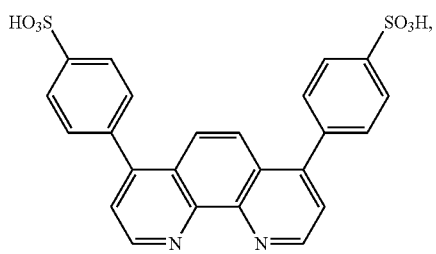
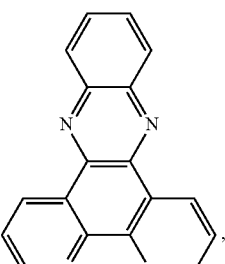
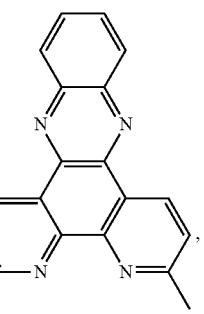
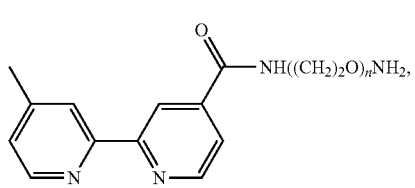
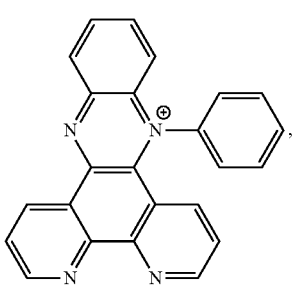
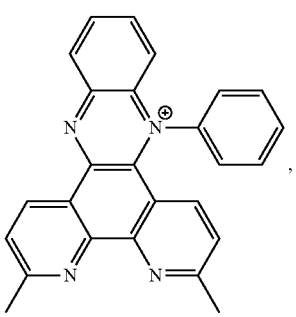
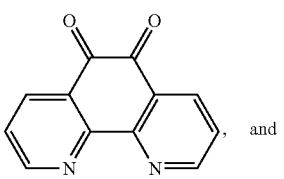
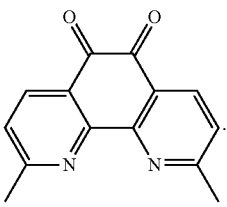
, and
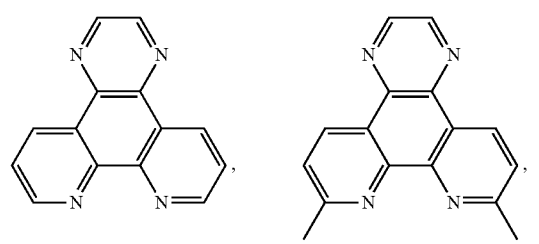
.
In some embodiments the compound comprises a structure according to at least one of the following formula:

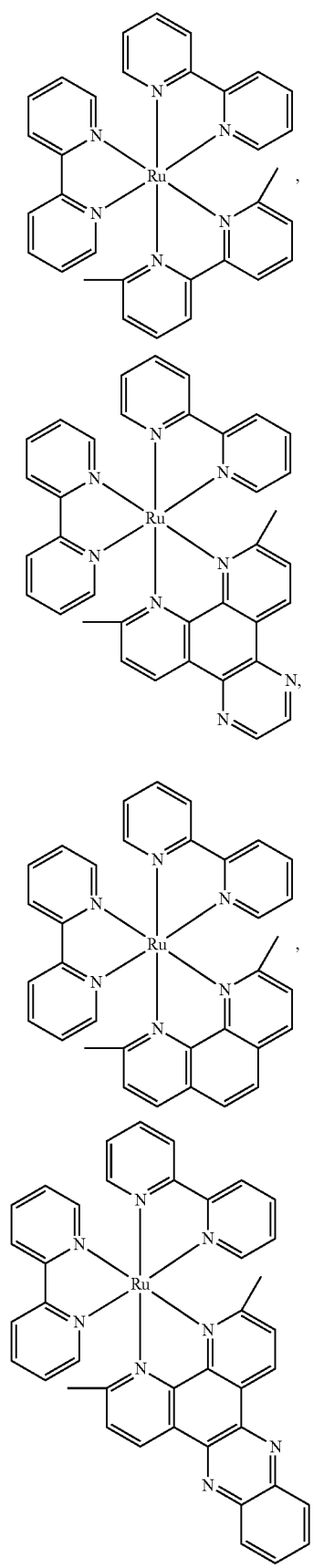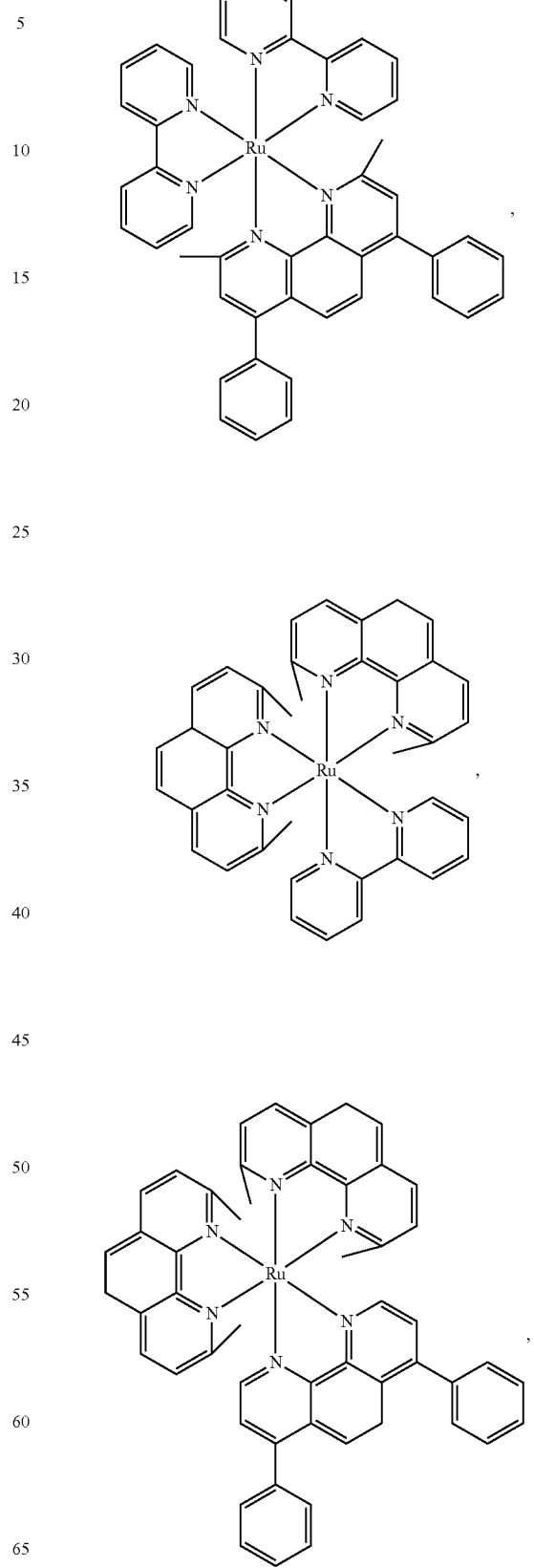

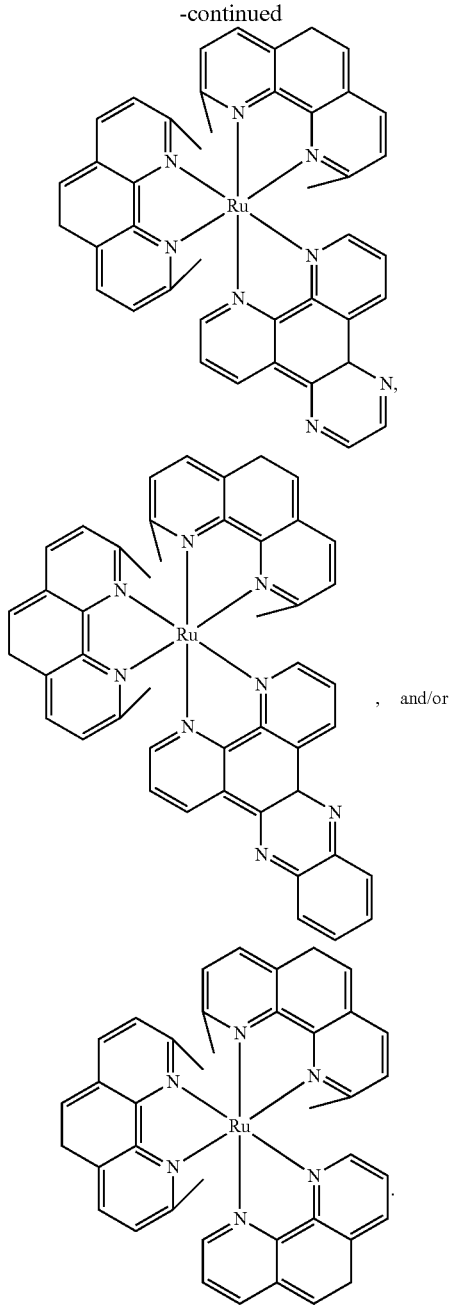

, and/or

In some embodiments the light-activated properties of the compounds can be tuned based on the selection of ligands and/or substituents, and the compounds can be tuned to be photo-activated (i.e., release ligands) when exposed to light having particular wavelengths. In this regard, the term "light" is used herein to refer to any electromagnetic radiation that can activate a compound. In some embodiments light includes ultraviolet light, visible light, near infrared light (NIR), or infrared light (IR). Compounds activated by relatively long wavelength light may be particularly well suited for targeting tumors and the like that are deep in tissues, since light generally penetrates deeper into tissues as the wavelength increases. Some embodiments of compounds have the surprising and unexpected advantage of being photo-activated by light having wavelengths greater than 500 nm.

More specifically, light can refer to electromagnetic radiation having a wavelength of about 350 nm to about 500 nm. In other embodiments light includes energy having a wavelength of about 500 nm to about 1000 nm. In specific embodiments light can refer to energy having a wavelength of about 300 nm, about 350 nm, about 450 nm, about 500 nm, about 550 nm, about 600 nm, about 650 nm, about 700 nm, about 750 nm, about 800 nm, about 850 nm, about 900 nm, about 950 nm, or about 1000 nm. In other specific embodiments light can refer to energy having a wavelength greater than about 300 nm, greater than about 350 nm, greater than about 450 nm, greater than about 500 nm, greater than about 550 nm, greater than about 600 nm, greater than about 650 nm, greater than about 700 nm, greater than about 750 nm, greater than about 800 nm, greater than about 850 nm, greater than about 900 nm, or greater than about 950 nm.

Still further, some embodiments of compounds also comprise a targeting agent and/or a therapeutic agent. Folate, estrogen, and eroltinib are examples of a targeting agent that can be used in embodiments of the presently-disclosed compounds. Those of ordinary skill will appreciate other small molecule targeting agents that can be incorporated into the present compounds. Additionally, hydroxyquinoline is an example of a therapeutic agent that can be used in embodiments of the presently-disclosed compounds. In some embodiments the photo-releasable ligands of the embodied compounds can be a targeting agent and/or a therapeutic agent.

The presently-disclosed compounds can further comprise an overall charge. In some embodiments the overall charge is −6 to +6. The overall charge can depend on the ligands incorporated into embodied compounds. For example, in some embodiments ligands comprising carboxylic acid and/or sulfonic acid result in compounds that have negative (e.g., −2) overall charges at physiological pH. In specific embodiments the present compounds comprise an overall charge of −6, −5, −4, −3, −2, −1, neutral charge, +1, +2, +3, +4, +5, or +6. Those of ordinary skill will appreciate that depending on the ligands of the present compounds, the overall charge may also be less than about −6 or greater than about +6.

The presently-disclosed subject matter further includes pharmaceutical compositions of the compounds as disclosed herein, and further includes a pharmaceutically-acceptable carrier. In this regard, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

The presently-disclosed subject matter further includes a kit that can include a compound/or pharmaceutical composition as described herein, packaged together with a device useful for administration of the compound or composition. As will be recognized by those or ordinary skill in the art, the appropriate administration aiding device will depend on the formulation of the compound or composition that is selected and/or the desired administration site. For example, if the formulation of the compound or composition is appropriate for injection in a subject, the device could be a syringe. For another example, if the desired administration site is cell culture media, the device could be a sterile pipette.

In some embodiments a kit can comprise one of the present compounds and/or pharmaceutical compositions thereof as well as a device for activating the compound or pharmaceutical composition. In some embodiments the device is a light-emitting device that emits light having at least a wavelength that can activate the compound or pharmaceutical composition. Accordingly, the device can be capable of emitting light having at least a wavelength of 500 nm or more, and in some instances a wavelength in a range of about 500 nm to about 1100 nm. In certain embodiments the device is a laser.

Still further, the presently-disclosed subject matter includes a method for treating cancer. In some embodiments the method comprises administering a compound, including one of the compounds described herein, to a subject in need thereof, and then exposing a site of the subject to light after the compound has been administered. As described above, the light in some embodiments can be a light having a wavelength of about 350 nm to about 1000 nm.

The term "administering" refers to any method of providing a compound and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition (e.g., cancer, tumors, etc.). In further various aspects, a preparation can be administered prophylactically; that is, administered for prevention of a disease or condition.

In some embodiments a subject will be administered an effective amount of the compound. In this respect, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Additionally, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

In some embodiments the subject in need thereof will be suffering or will have been diagnosed with one or more neoplastic or hyperproliferative diseases, disorders, pathologies, or conditions. Thus, a site to be exposed in a subject may be in close proximity or at the location of such a disease, condition, etc. (e.g., tumor). Examples of such diseases, conditions, and the like include, but are not limited to, neoplasms (cancers or tumors) located in the colon, abdomen, bone, breast, digestive system, esophagus, liver, pancreas, peritoneum, endocrine glands (adrenal, parathyroid, pituitary, testicles, ovaries, cervix, thymus, thyroid), eye, head and neck, nervous (central and peripheral), lymphatic system, pelvis, skin, soft tissue, spleen, thoracic areas, bladder, and urogenital system. Other cancers include follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer, or metastases thereof.

A subject may also be in need thereof because they have acquired diseases or conditions associated with abnormal and increased cell survival such as, but are not limited to, progression and/or metastases of malignancies and related disorders such as leukemia (including acute leukemias (e.g., acute lymphocytic leukemia, acute myelocytic leukemia, including myeloblastic, promyelocytic, myelomonocytic, monocytic, and erythroleukemia) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. The conditions, diseases, and the like described above, as well as those that will be apparent to those of ordinary skill in the art, are collectively referred to as "cancer" herein.

The terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

With regard to the step of exposing a site, the method of exposing can be modified to meet the needs of a particular situation. Accordingly, the light can be sunlight, photo-optic light, or laser light, and thus the light can be ultraviolet light, visible light, near infrared light, or infrared light, for example. The light can be exposed from a laser light source, a tungsten light source, a photooptic light source, and the like. Light can also be exposed in at relatively specific sites, and therefore can be exposed by the use of laser technology, fibers, probes, tubes, and the like. Such probes, fibers, or tubes can be directly inserted, for example, into a body cavity or opening of a subject, or under or through the skin of a subject, to expose the compounds that have been administered to light.

It will be appreciated that embodiments of the presently-disclosed subject matter resolve the unmet needs in the art, including specific embodiments of strained Ru(II) polypyridyl complexes that utilize the steric clash of their ligands to promote visible light mediated ligand expulsion. While unreactive in the dark, these exemplary compounds are transformed upon light activation into potent cytotoxic species. As potential PDT agents, these compounds offer key advantages, including ease of synthesis, high solubility, low dark toxicities, and resistance to inactivation by thiol reagents. In certain embodiments, the DNA damaging mechanism appears to mimic the activity of cisplatin, which would make them potentially amenable to a variety of cancer types, and also can have greater potency than cisplatin.

EXAMPLE

The presently-disclosed subject matter is further illustrated by the following specific but non-limiting example. The example may include compilations of data that are representative of data gathered at various times during the course of development and experimentation related to the presently-disclosed subject matter.

Example 1

In this Example two heteroleptic complexes were synthesized containing one and two biquinoline (biq) ligands, and one or two smaller, non-strained 1,10-phenanthroline (phen) ligands, as shown in FIG. 1. The synthesis and purification was performed under low ambient light in order to avoid photo-decomposition. The addition of the biq ligands resulted in bathochromic shifts in the absorption spectra, as compared to Ru(phen)$_3$, a prototypical Ru(II) polypyridyl complex with a $\lambda_{max}$=450 nm for the low energy MLCT absorption. As shown in FIG. 1, addition of one biquinoline ligand in 1 shifts the MLCT to lower energies, with $\lambda_{max}$=525 nm. Incorporation of two biquinoline ligands further shifts the $\lambda_{max}$ to 550 nm for 2. Expansion of the region from 600-900 nm shows that there is some absorption at 700 nm for 1, while 2 is able to absorb light up to 800 nm.

Figure 2:
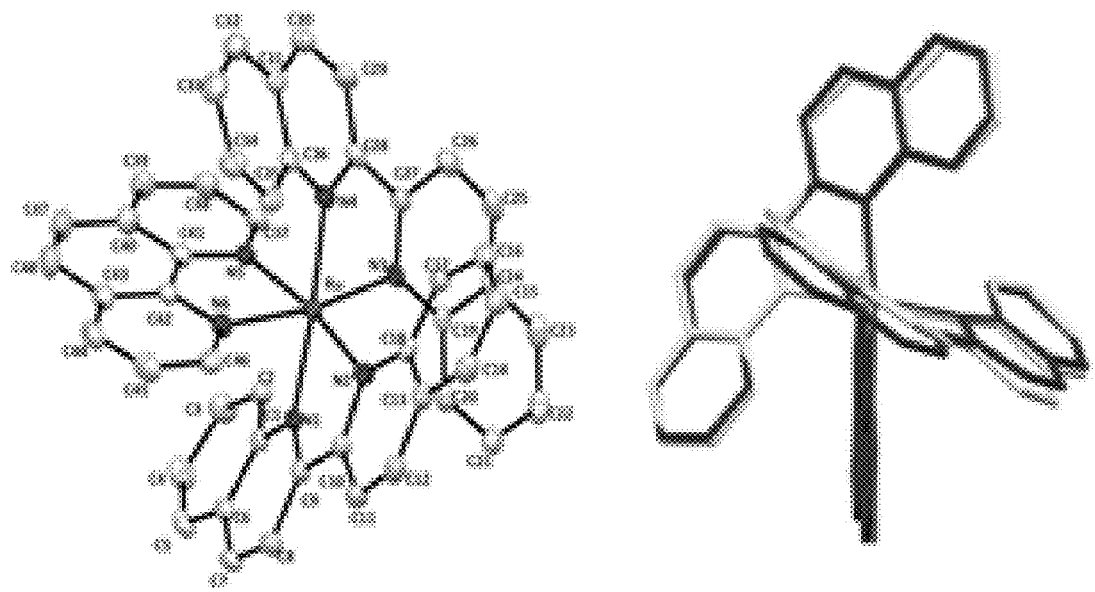
FIG. 2 includes images showing an ellipsoid plot (at 50% probability) of 2 (left) and a capped stick overlay of 2 (right). Both biquinoline ligands have a 20° bend from the ideal octahedral plane, where the N(3)-N(4) biquinoline has a 12° twist about the C—C bond between the two quinolones and the N(1)-N(2) biquinoline does not.
Figure 3:
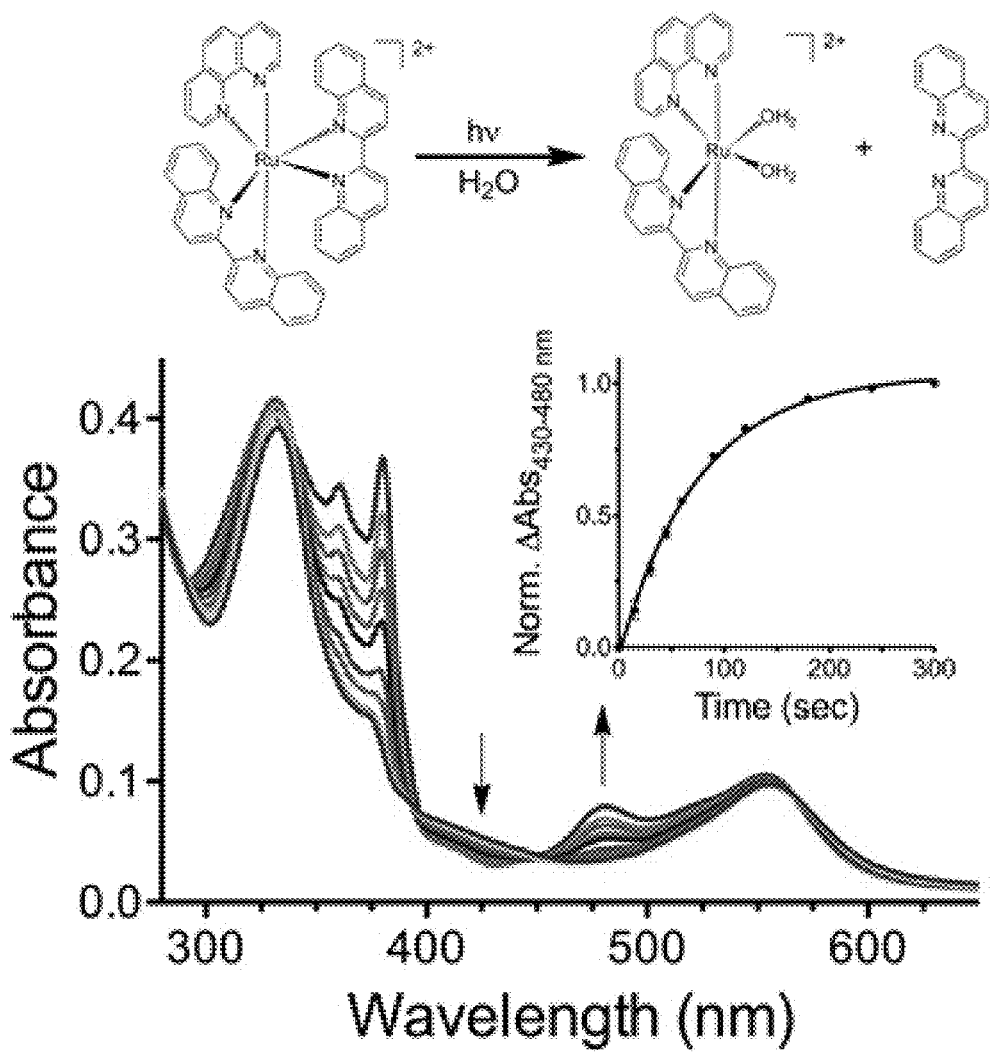
FIG. 3 includes a reaction scheme showing the photosubstitution reaction of 2 in $H_2O$, and further includes charts showing the associated UV/Vis absorption spectra at different time points in the reaction under blue light, where the inset shows the kinetic fit for the reaction.
Figure 4A:
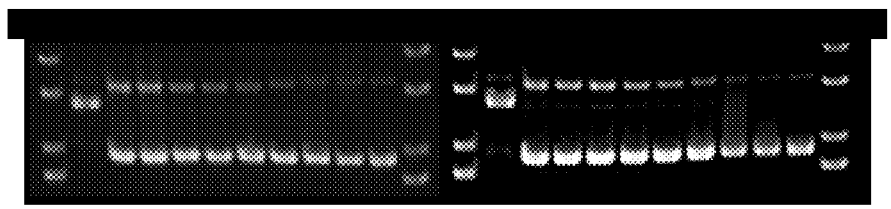
FIGS. 4A to 4E includes images showing agarose gel electrophoresis for the dose response of 1 (left) and 2 (right) with 40 μg/mL pUC19 plasmid in the (Figure A) dark and after irradiation with (FIG. 4B) blue (>400 nm), (FIG. 4C) green (>450 nm), (FIG. 4D) red (>600 nm), and (FIG. 4E) near-IR (>650 nm) light. Lane 1: DNA ladder; Lane 2: EcoRI; Lane 3: $Cu(OP)_2$; Lane 4: 0 μM; Lane 5: 15 μM; Lane 6: 30 μM; Lane 7: 60 μM; Lane 8: 125 μM; Lane 9: 250 μM; Lane 10: 500 μM; Lane 11: 1,000 μM; Lane 12: DNA Ladder.
Figure 4B:
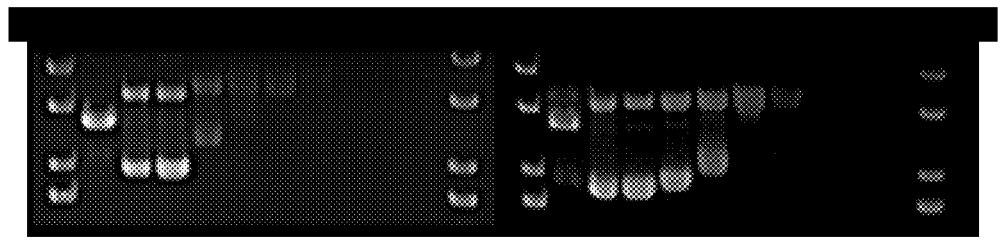
Figure 4C:
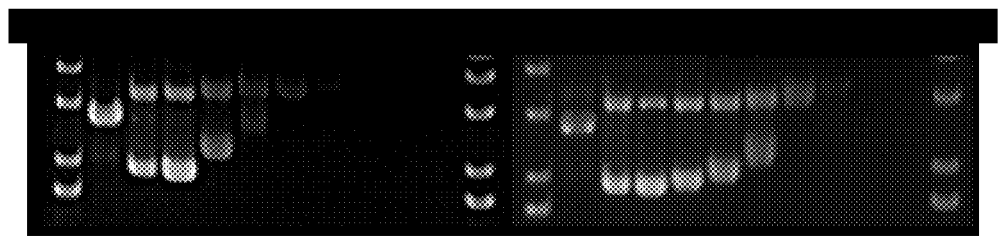
Figure 4D:
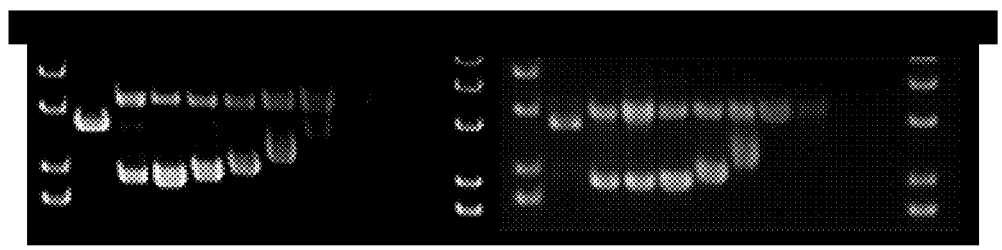
Figure 4E:
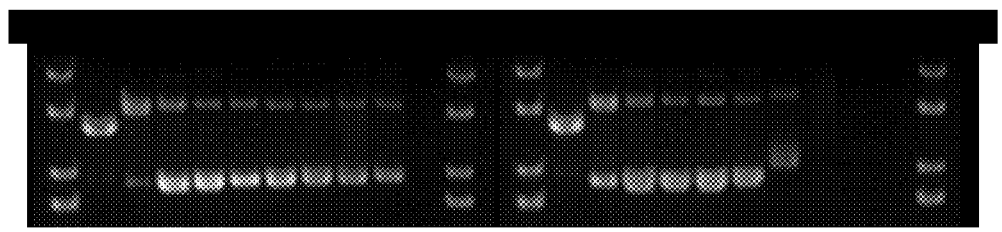

Analysis of the crystal structures for the biquinoline complexes provided a means to compare the extent of distortion in the ground state structures. The deformation of the octahedral geometry was manifest in lengthening of the bonds between the metal and the ligand as well as twisting of the ligands (FIG. 2). In comparison with Ru(phen)$_3$, an undistorted octahedral complex with average Ru—N bond lengths of 2.064 Å, compound 2 was slightly distorted with the Ru—N bonds lengthened to 2.08-2.10 Å, as shown in FIG. 2 and Table 1. In compound 1, one of the phenanthroline ligands maintains an average length similar to that of Ru(phen)$_3$ at about 2.060 Å, while the other two ligands' Ru—N bonds are lengthened to an average of 2.11 and 2.09 Å. The biquinoline in 1 was twisted by 5° about the C—C bond between the two quinoline systems. In contrast, the two biquinoline ligands showed different distortions in compound 2, with biq(2) exhibiting a 12.1(4)° twist, while biq(1) has a 2.7(4)° rotation. The biquinolines are also bent out of the normal plane by approximately 20° in both complexes, while the phenanthroline ligands stay in the plane. This bend out of plane tips the biquinoline toward the phenanthroline ligand for 2, creating a 7° increase in the angle between the biquinoline ligands, as well as an 8° and 10° compression in the biquinoline-phenanthroline angle. In contrast, the biquinoline ligand in compound 1 pushes the two phenanthroline ligands toward each other by 8°. In both structures the biquinoline ligands maximize the space around them, which induces the distortion in complexes 1 and 2.

well with the absorption spectra, with rapid reaction observed with blue and green light, while slower ejection kinetics occurred with red and near-IR light. The most rapid ejection was observed with blue light for complex 2, as shown in FIG. 3, with a $t_{1/2}$ of 53 seconds. A $t_{1/2}$ of 8.7 minutes was measured for 1.

The presence of isosbestic points in the absorption spectra indicated the direct conversion from starting material to a single product. Samples of each complex after light activation were subjected to analytical HPLC. The tris-polypyridyl compounds are converted to bis-polypyridyl complexes with the selective ejection of a biquinoline ligand in all cases, as indicated by the peak with a retention time of 32.1 minutes (identified as the free biquinoline ligand). The phenanthroline ligand was not observed in any of the chromatograms, and the only free ligand that was detected in the mass spectra for all samples was biquinoline. Without being bound by theory, the selective labilization of the biquinoline indicates that the distortion due to the twisting of the ligand may drive the ejection process, the breaking of the Ru-ligand bonds proceeds through a step-wise mechanism, and fused ring systems such as phenanthroline may re-coordinate the metal, preventing ligand loss. The quinoline rings in the biquionline ligand can rotate about the $C_2$-$C_{2'}$ bond, inhibiting re-coordination.

The ability of the ruthenium complexes to damage DNA upon light activation was determined by gel electrophoresis with supercoiled pUC19 plasmid, as shown in FIG. 4. All complexes induced a dose-dependent effect on the DNA mobility, with increasing retention indicating photobinding of the complex to the plasmid DNA. The decreased migration on the gel with increasing concentration of complex is consistent with a DNA crosslinking effect. It should be noted that intercalation also causes decreased migration in agarose gels, but as the effect was not observed for 1 and 2 in the absence of light, intercalation of the compounds is unlikely. Similar results were obtained for Ru(phen)$_2$(H$_2$O)$_2$, which covalently modifies DNA.

The compounds did not appear to photocleave DNA, as no increase in the linear or relaxed circle forms of DNA were observed. A significant loss of the ethidium bromide (EtBr) signal was observed for the light activated 1, 2, and

TABLE 1

Selected bond lengths (Å), bond angles (°), and torsion angles (°) for compounds 1 and 2.

| Compound 1 | | Compound 2 | |
|---|---|---|---|
| Ru—N$_{1\text{-}biq}$ | 2.112(3) | Ru—N$_{1\text{-}biq(1)}$ | 2.084(2) |
| Ru—N$_{2\text{-}biq}$ | 2.095(3) | Ru—N$_{2\text{-}biq(1)}$ | 2.079(2) |
| Ru—N$_{3\text{-}phen(1)}$ | 2.063(3) | Ru—N$_{3\text{-}biq(2)}$ | 2.088(2) |
| Ru—N$_{4\text{-}phen(1)}$ | 2.056(3) | Ru—N$_{4\text{-}biq(2)}$ | 2.093(2) |
| Ru—N$_{5\text{-}phen(2)}$ | 2.091(3) | Ru—N$_{5\text{-}phen}$ | 2.104(3) |
| Ru—N$_{6\text{-}phen(2)}$ | 2.091(3) | Ru—N$_{6\text{-}phen}$ | 2.098(2) |
| N$_{2\text{-}biq}$—Ru—N$_{3\text{-}phen(1)}$ | 99.15(12) | N$_{2\text{-}biq(1)}$—Ru—N$_{3\text{-}biq(2)}$ | 97.14(10) |
| N$_{4\text{-}phen(1)}$—Ru—N$_{5\text{-}phen(2)}$ | 82.75(12) | N$_{4\text{-}biq(2)}$—Ru—N$_{5\text{-}phen}$ | 80.14(9) |
| N$_{1\text{-}biq}$—Ru—N$_{2\text{-}biq}$—C$_{10\text{-}biq}$ | −20.72(4) | N$_{1\text{-}biq(1)}$—Ru—N$_{2\text{-}biq(1)}$—C$_{10\text{-}biq(1)}$ | −20.41(19) |
| N$_{1\text{-}biq}$—C$_{9\text{-}biq}$—C$_{10\text{-}biq}$—N$_{2\text{-}biq}$ | −5.62(5) | N$_{1\text{-}biq(1)}$—C$_{9\text{-}biq(1)}$—C$_{10\text{-}biq(1)}$—N$_{2\text{-}biq(1)}$ | 2.7(4) |
| | | N$_{4\text{-}biq(2)}$—Ru—N$_{3\text{-}biq(2)}$—C$_{27\text{-}biq(2)}$ | −19.5(2) |
| | | N$_{3\text{-}biq(2)}$—C$_{27\text{-}biq(2)}$—C$_{28\text{-}biq(2)}$—N$_{4\text{-}biq(2)}$ | 12.1(4) |

The complexes all underwent photo-substitution reactions upon exposure to visible light. The kinetics of the ejection process were followed by absorption spectroscopy, as shown in FIG. 3. The number of sterically hindered ligands and the corresponding distortion in the complex affected the rate of the photosubstitution reaction, with an order of magnitude variation in $t_{1/2}$ for the different structures. The wavelength dependence of the photochemical process also correlated Ru(phen)$_2$(H$_2$O)$_2$ at concentrations above 15 µM. To determine if this signal loss was due to degradation of the DNA, bands were excised, purified and quantified for DNA content. Approximately 80% of the plasmid was recovered from the excised bands, despite a 98% reduction of the EtBr signal. Without being bound by theory, this suggests that the ruthenium interferes with the EtBr emission and/or the structure of the ruthenium modified DNA prevents intercalation. The purified DNA exhibited the same decreased mobility pattern when subjected to a second agarose gel, supporting a covalent, photobinding mechanism for 1 and 2. This may provide an advantage over DNA photocleavage mediated by PDT agents and other metal complexes that require oxygen and generate single strand breaks, which may be readily repaired.

The photoreactivity of 1 and 2 was dependent on the wavelength of light used. Significant activity was retained upon shifting to both red and near-IR light, as indicated by gel shift. It should be noted, however, that the light intensity is significantly attenuated by the longer wavelength cut-off filters (e.g., >600 nm). There is also diminished molar absorptivity for the compounds in the red and near-IR region. Thus, more intense red or near-IR light sources likely would increase the apparent potency of the compounds. This is supported by the fact that irradiation for longer times induced greater DNA photobinding. Both complexes showed negligible reactivity with the DNA in the dark.

Cytotoxicity studies were performed to determine if the light-induced DNA damage translated to biological activity in cancer cells. The complexes exhibited dose dependent cytotoxicity in the HL-60 human leukemia cell line. The activity of the compounds was also dependent on the light dose, indicating that light-activation is correlated with cytotoxicity. The compounds were incubated with the cells for 12 hours prior to irradiation with blue (>400 nm), red (>600 nm), and near-IR (>650 nm) light (Table 2). This potency is comparable to cisplatin, which was found to have an $IC_{50}$ value of 3.1 µM. Increasing the light dose increased the observed potency. For example, compound 2 showed a 2-fold enhancement in potency upon increasing the irradiation time from 3 to 6 minutes with red light, recovering the activity measured under irradiation with blue light. The superior activity of 2 compared to 1 with red and near-IR light irradiation is consistent with the presence of a longer wavelength absorption feature extending past 700 nm. A phototoxicity index (PI) value (the toxicity in the dark vs. the light) of 43 was found with blue light for compound 1. Compound 2 was more potent than 1 with red- and near-IR light, exhibiting a PI of 20 and 9.2, respectively.

flash chromatography, and converted to chloride salts for testing.

Materials and General Methods

All chemicals for this Example were obtained from commercial sources and were used without further purification. $Ru(bpy)_2Cl_2 \cdot 2H_2O$ was purchased from Strem Chemicals Inc. (Newburyport, Mass.) and 5-aminolevulinic acid hydrochloride (ALA) was purchased from Alfa Aesar (Ward Hill, Mass.).

All $^1H$ NMR were obtained on a Varian Mercury spectrometer (400 MHz; Palo Alto, Calif.) and chemical shifts reported relative to the residual solvent peak of acetonitrile at δ 1.93. The $^{13}C$ chemical shifts are reported relative to $CD_3CN$ at δ 1.39. Electrospray ionization (ESI) mass spectra were obtained on a Varian 1200L mass spectrometer. Absorption spectra were obtained on an Agilent 8453 Diode Array spectrophotometer (Santa Clara, Calif.). Photoexpulsion experiments were performed using a Dell 200 Watt 1410X projector (for in vitro photoejection experiments) or 410 Watt 955 Model 900 AJH projector (for cell cytotoxicity studies) (Dell Inc.; Round Rock, Tex.) fitted with an Edmund Optics filter (NT43-935) (Barrington, N.J.). UV/Vis experiments were performed in a 1-cm pathlength quartz cuvette located 18 inches from the projector. Kinetics were fit using the equation for a single exponential with the Prism software package. Cell survival was quantified using a Tecan Spectroflur Plus Microplate Reader (Tecan Systems, Inc.; San Jose, Calif.).

Furthermore, chloride salts of the ruthenium complexes were injected on an Agilent 1100 Series HPLC equipped with a model G1311A quaternary pump, G1315B UV diode array detector and Chemstation software version B.01.03. Chromatographic conditions were optimized on a Column Technologies Inc. C18, 120 Å (250 mm×4.6 mm inner diameter, 5 µm) (Downers Grove, Ill.) fitted with a Phenomenex C18 (4 mm×3 mm) (Torrance, Calif.) guard column. 15 µL injection volumes of 30 µM solutions of the complex were used. The detection wavelength was 280 nm. Mobile phases used were 0.1% formic acid in $dH_2O$ and 0.1% formic acid in HPLC

TABLE 2

Photobiological activity in HL-60 cells.

| Compound | $\lambda_{abs}$/nm ($\epsilon$/M$^{-1}$cm$^{-1}$) | IC$_{50}$ [µM] | | | | | Phototoxicity Index (PI) | |
|---|---|---|---|---|---|---|---|---|
| | | Dark | Blue (3 min) | Red (3 min) | Red (6 min) | IR (25 min) | Blue | IR |
| 1 | 525 (8,300) | 52.5 | 1.22 | 13.8 | 7.63 | 15.8 | 43 | 3.32 |
| 2 | 550 (4,950) | 47.3 | 2.4 | 4.54 | 2.29 | 5.14 | 19.7 | 9.2 |
| Cisplatin | | 3.1 | 3.1 | N.D. | N.D. | N.D. | 1 | N.D. |

Example 2

In this Example three complexes with structural differences were explored to test the strain-mediated photoactivation approach (Table 3). The complexes were synthesized and characterized as a racemic mixture of Λ and Δ enantiomers. $Ru(bpy)_2phen$ (3) was used as an unstrained control. In order to distort the geometry about the octahedral metal center, polypyridyl ligands with methyl substituents were incorporated into the Ru(II) complexes; these groups are directed towards the other coordinating ligands, causing steric clashes. The complexes were readily prepared under low light conditions by refluxing the precursor $Ru(bpy)_2Cl_2$ with the desired ligand in ethylene glycol. They were purified by silica gel grade acetonitrile (Fisher Brand; Pittsburgh, Pa.). The gradient is shown in the table below.

| Time (minutes) | 0.1% formic acid in dH$_2$O | 0.1% formic acid in MeCN |
|---|---|---|
| 0 | 98 | 2 |
| 2 | 95 | 5 |
| 5 | 70 | 30 |
| 15 | 70 | 30 |
| 20 | 40 | 60 |
| 30 | 5 | 95 |
| 35 | 98 | 2 |
| 40 | 98 | 2 |

All metal complexes were synthesized and handled in low ambient light. The metal complexes were converted to the chloride salts prior to biological testing to increase water solubility. The ion exchange was accomplished by precipitation of the complex from dry acetone by the addition of tetrabutylammonium chloride. The compounds were filtered and stored in the dark. The synthesis of the 2,9-dimethyl dpq ligand was performed according to known procedures.

Compound 4: $Ru(bpy)_2Cl_2 \cdot 2H_2O$ (200 mg, 0.384 mmol) and 6,6'-dimethyl-2,2'-bipyridine (78 mg, 0.423 mmol) were added to 8 mL of degassed ethylene glycol in a pressure tube. The mixture was heated in the dark for 6 hours, allowed to cool and poured into 50 mL of distilled water. Addition of a saturated aq. $KPF_6$ solution produced a dark orange precipitate that was collected by vacuum filtration. The purification of the solid was carried out by flash chromatography (silica gel, 0.1% saturated $KNO_3$, 2% $H_2O$ in MeCN ramped to 9% $H_2O$) to give the pure complex. A saturated aq. solution of $KPF_6$ was added, and the metal complex was extracted into $CH_2Cl_2$. It was dried down to give a red solid. Yield: 297 mg (87%).

Compound 5: $Ru(bpy)_2Cl_2 \cdot 2H_2O$ (200 mg, 0.384 mmol) and 2,9-dimethyldpq (150 mg, 0.577 mmol) were added to 8 mL of degassed ethylene glycol in a 15 mL pressure tube. The mixture was heated with stirring in the dark for 6 hours. The dark red solution was allowed to cool and poured into 50 mL of distilled water. Addition of a saturated aq. $KPF_6$ solution produced a dark orange precipitate that was collected by vacuum filtration. The purification of the solid was carried out by flash chromatography (silica gel, 0.1% saturated $KNO_3$, 2% $H_2O$ in MeCN ramped to 9% $H_2O$) to give the pure complex. A saturated aq. solution of $KPF_6$ was added, and the metal complex was extracted into $CH_2Cl_2$. It was dried down to give a red solid. Yield: 284 mg (77%).

Compound 6: $Ru(bpy)_2phen$.

Photoejection

Figure 5:
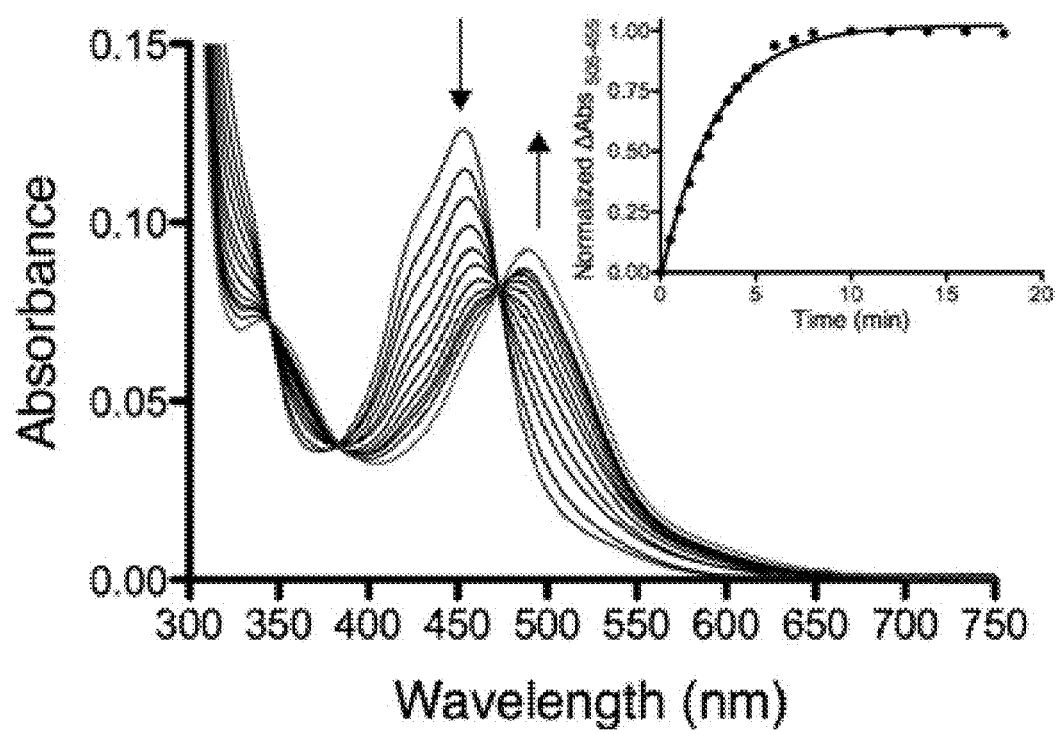
FIG. 5 includes charts showing the UV/Vis absorption of 4 following photoejection in buffer (10 mM phosphate buffer, pH 7.5), where the inset shows the photoejection kinetics.

It was observed that addition of the methyl groups to either bpy (2,2'-bipyridyl) or the DNA intercalating ligand dpq (dipyrido[3,2-f:2',3'-h]-quinoxaline) results in complexes that undergo photochemical reactions upon exposure to light. Irradiation of 4 and 5 in either acetonitrile or buffer with >450 nm light using a 200 W projector and cut-off filters resulted in substitution of solvent molecules for the polypyridyl ligand. The photochemical reaction was conveniently followed by UV/Vis absorption spectroscopy, as shown in FIG. 5.

The photo-ejection is both rapid and selective, with a $t_{1/2}$ of 2 minutes for 4 and clear isosbestic points at 351, 389, and 476 nm, highlighting the selectivity of the photo-labilization. ESI-MS experiments identified the ejection of the 6,6'-dimethyl-2,2'-bpy ligand from compound 4, while compound 5 ejects the 2,9-dimethyl-dpq ligand. The reaction went to completion for 4. The reaction kinetics are 30-fold faster for 4 than for 5, possibly due to the rigidity of the dpq ligand that may enhance re-chelation, interfering with the stepwise dissociative bond breaking mechanism that releases the ligand. Control compound 3 was photo-stable under the irradiation conditions used. All complexes were stable the dark in aqueous solution at concentrations of 50 mM for months at room temperature.

Biological Procedures

Plasmid-compound gel analysis: Plasmid pUC19 was obtained from Bio-Rad (Hercules, Calif.), transformed into DH5a cells and positive transformants were selected by colony formation on Ampicillin LB-Agar plates. Colonies were grown in LB and plasmid isolated using a Maxi-prep plasmid isolation kit (Qiagen; Velno, Netherlands). Plasmid amounts were quantified by UV/VIS. For dosing studies, 40 µg/ml of plasmid was incubated with compound dosed from 0 to 500 µM in 96 well plates. They were incubated for 30 min prior to light activation for 1 hour using a Dell 1410x 200 W projector fitted with a >450 nm cut-off filter. Dark controls were performed by keeping the DNA:compound mixtures in the dark. The samples were incubated overnight after light activation before gel analysis; the dark samples were also incubated for the same time period. Linear plasmid and relaxed circle plasmid were generated and run side-by-side with compound treated samples. Linear plasmid was generated using the EcoRI restriction enzyme (New England BioLabs; Ipswich, Mass.) following the manufacturers protocol. Single cut, relaxed circle, plasmid was generated using the copper phenanthroline reaction. Reaction was carried out in 10 mM phosphate buffer pH 7.5, with 40 µg/ml plasmid, 1 mM DTT, 1 mM hydrogen peroxide, and 5 µM copper phenanthroline for 30 min at 25° C. The addition of DTT reduced the copper phenanthroline to the +1 charge state, followed by reaction with peroxide created the damage to the DNA. Samples were resolved on a 1% non-EB (ethidium bromide) agarose gel followed by 40 minutes of staining with 0.5 µg/ml EB in Tris-Acetate buffer followed by 40 minutes of destaining in Tris-Acetate before imaging.

Glutatione Assay:

The pUC19 plasmid was incubated at 25 µg/ml with 30 mM of either compound 4 or cisplatin nitrate in 10 mM phosphate buffer pH 7.5, with increasing amounts of glutathione (GSH) at 25° C. Cisplatin (30 µM) and compound 4 (30 µM) were co-dosed with increasing concentrations of GSH. The concentrations of GSH were 0.01, 0.1, 1, 10, 40 mM, giving a molar ratio between the compounds and glutathione of a) 1:0.3, b) 1:3.3, c) 1:33, d) 1:333, e) 1:1333. Compound 4 was activated with light for 1 hr as described above followed by a 12 hr incubation in the dark, while cisplatin nitrate was incubated with plasmid and GSH in the dark for 12 hrs. Control reactions with pUC19 in the presence and absence of GSH were carried out for 12 hrs in the dark with 25 µg/ml plasmid and 40 mM GSH in 10 mM phosphate buffer, pH 7.5. The plasmid was resolved on a 1% agarose gel as described above.

The results of the gel electrophoresis are shown in FIG. 6. Cisplatin kinked DNA and caused unwinding, reducing its mobility on agarose gels and impeding intercalation of EtBr. $Cu(phen)_2$ produced single strand breaks, generating relaxed circular plasmid DNA. Exposure of ruthenium compounds 3-5 to visible light (200 W, 1 hour) in the presence of pUC19 plasmid produced both effects: DNA photocleavage (in the case of compound 3), and DNA photobinding, which may be crosslinking (in the case of 4). Compound 5 exhibited a combination of these two mechanisms. Light-induced DNA single strand breaks produced by 3 are shown as the conversion of supercoiled DNA to relaxed circular form (FIG. 6A). DNA photobinding for 4 and 5 is evidenced by the supercoiled DNA that migrated more slowly through the gel and EtBr intercalation was diminished with increasing concentration of the Ru(II) complexes (FIGS. 6B and 6C). An additional form was observed with high concentrations of 5 that migrated more quickly that the relaxed circular form (FIG. 6C lanes 8-10). Without light no DNA damage or binding was observed.

Figure 6A:
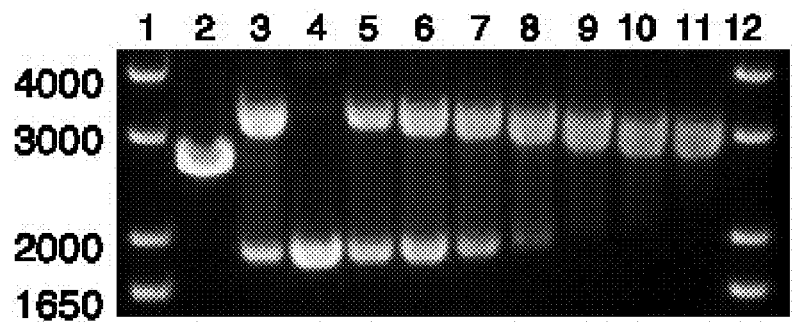
FIGS. 6A to 6D includes images showing agarose gels electrophoresis for 40 μg/mL pUC19 plasmid (10 mM phosphate buffer, pH 7.5) with (FIG. 6A) 3, (FIG. 6B) 4, and (FIG. 6C) 5, where Lanes 1 and 12: DNA molecular weight standard, Lane 2: linear pUC19, Lane 3: relaxed circle ($Cu(phen)_2$ reaction with pUC19), Lanes 4-11: 0, 7.5, 15, 30, 60, 120, 240, and 500 μM compound; and further includes agarose gel electrophoresis showing (FIG. 6D) Lanes 1 and 14: DNA molecular weight standard, Lane 2: pUC19, Lane 3: pUC19+ 40 mM GSH. Cisplatin (30 μM, lanes 4-8) and compound 4 (30 μM, lanes 9-13) were dosed with GSH: lanes 4-8 and 9-13: 0.01, 0.1, 1, 10, 40 mM GSH.
Figure 6B:
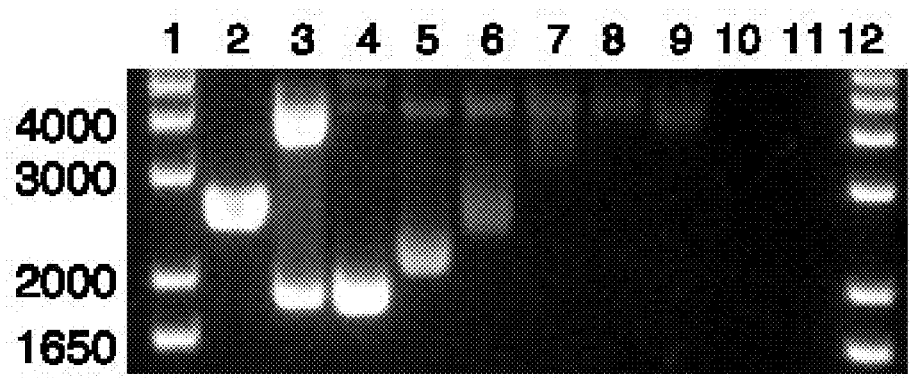
Figure 6C:
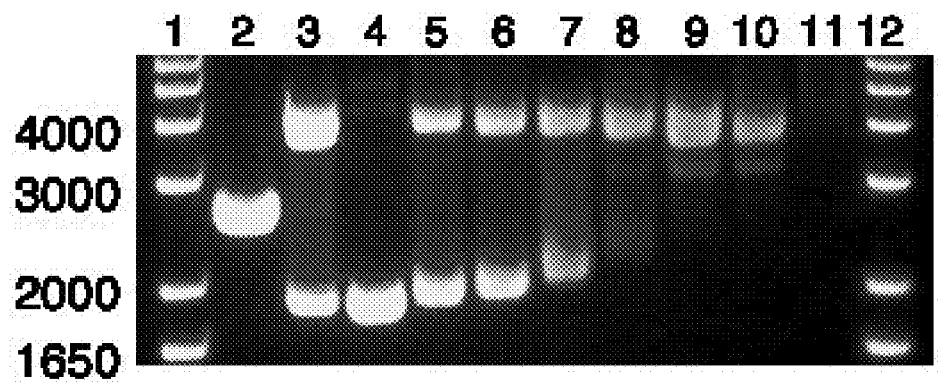
Figure 6D:
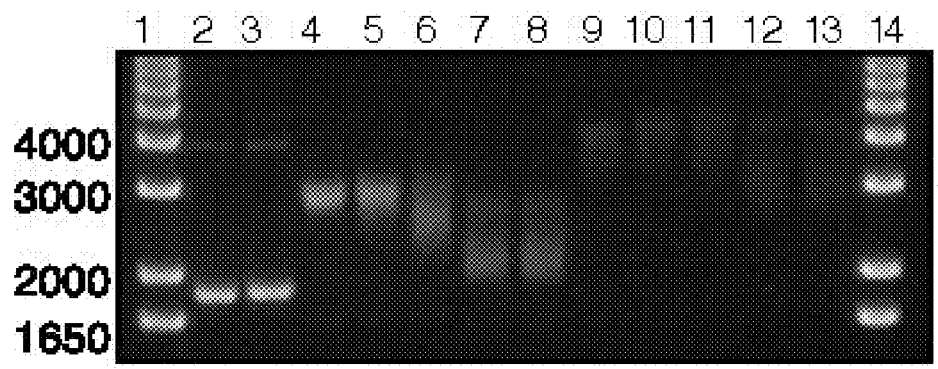
Figure 7A:
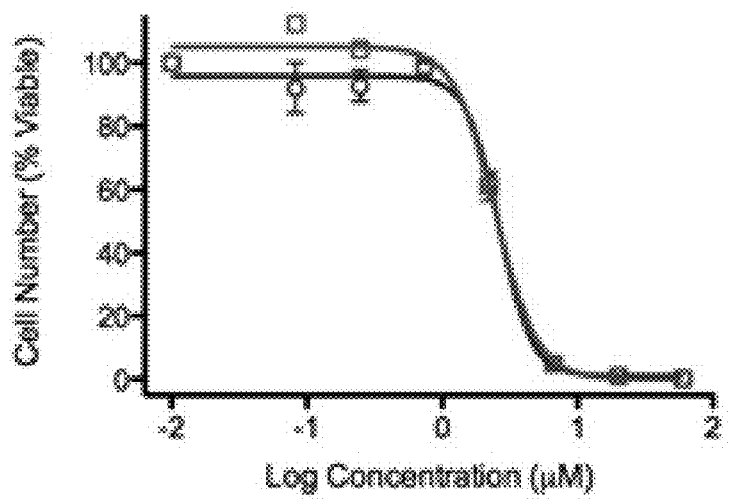
FIGS. 7A to 7D includes charts showing the cytotoxicity dose responses of metal complexes in HL60 cells for (FIG. 7A) cisplatin, (FIG. 7B) 3, (FIG. 7C) 4, and (FIG. 7D) 5. Dark conditions (circles); irradiated samples, 3 min>450 nm light (squares). (n=3).
Figure 7B:
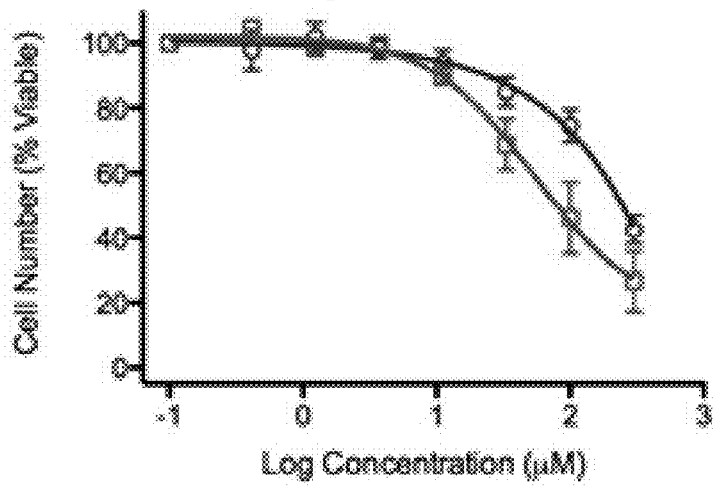
Figure 7C:
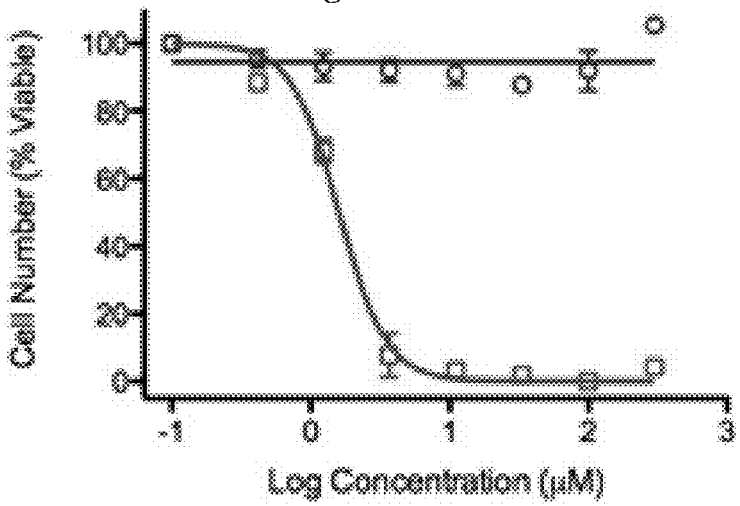
Figure 7D:
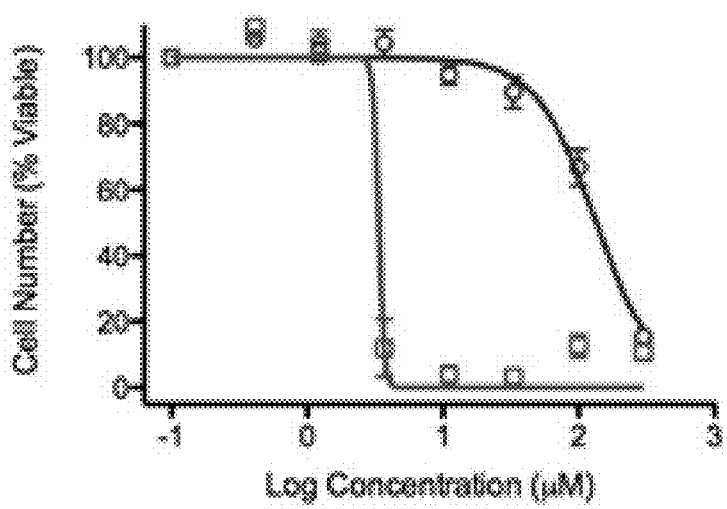
Figure 8A:
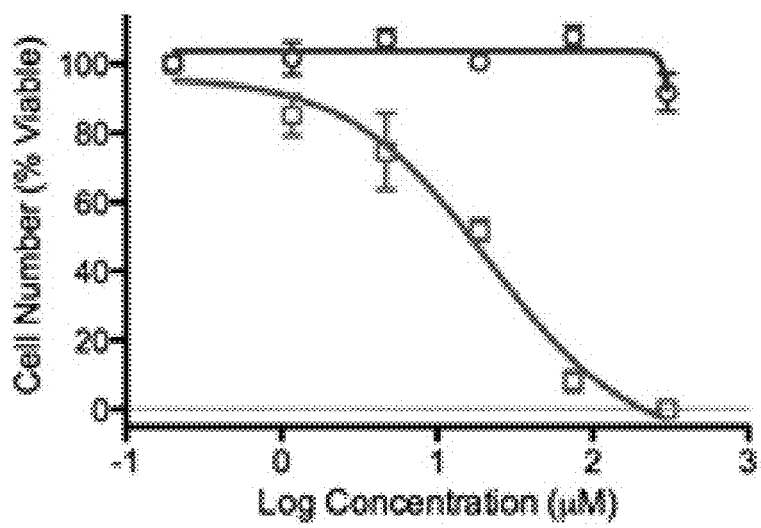
FIGS. 8A to 8B includes charts showing the cytotoxicity dose responses in A549 tumor spheroids for (FIG. 8A) compound 4 (dark conditions, circles; irradiated samples, 3 min>450 nm light, squares), and (FIG. 8B) cisplatin (dark conditions, squares; ALA, irradiated samples, 3 min>450 nm light, circles). (n=3.)
Figure 8B:
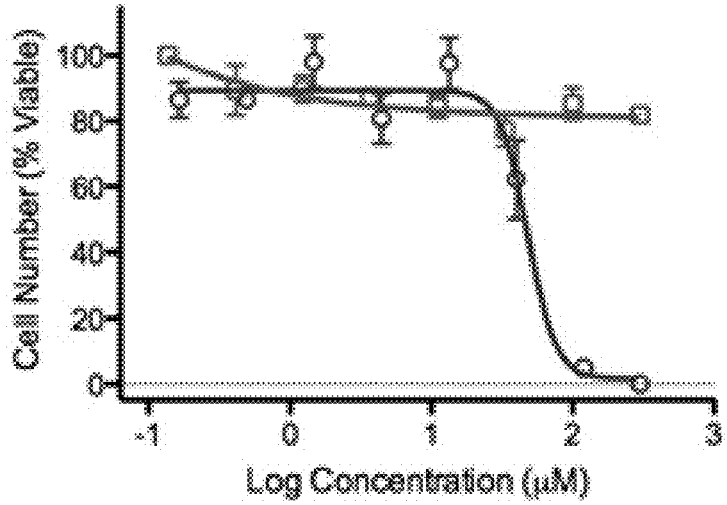

Unlike known agents, such as cisplatin, prodrug compounds 4 and 5 did not interact with GSH over a period of days, as observed by UV/Vis spectroscopy. The photoactivated DNA crosslinking $Ru(bpy)_2$ species retained its ability to damage DNA, even at higher GSH concentrations. FIG. 6D shows the crosslinking of plasmid DNA by cisplatin and light-activated compound 4 in the presence of increasing amounts of GSH. Cisplatin exhibited reduced crosslinking efficacy with increasing levels of GSH, as indicated by greater mobility of the DNA on the agarose gel. The active form of 4 caused greater DNA binding than cisplatin. As described below, cisplatin or compound 4 were co-dosed with increasing concentrations of GSH. GSH reduced cytotoxicity for cisplatin, but not for compound 4.

irradiation. In contrast, photoreactive compounds 4 and 5 showed light-triggered toxicity. After irradiation, both compounds 4 and 5 produced single µM $IC_{50}$ values (Table 3). The complexes were more potent than cisplatin when light activated and non-toxic in the dark, with dark $IC_{50}$ values over 100 µM for 5 and no dark toxicity observed up to a concentration of 300 µM for 4.

TABLE 3

Cytotoxicity $IC_{50}$ values in 2D and 3D cellular assays. The phototoxicity index (PI) is the ratio of the dark and light $IC_{50}$ values. The multicellular resistance (MCR) index is the ratio of the spheroid and monolayer culture $IC_{50}$ values.

| Compound | Light $IC_{50}$ [µM] | | | Dark $IC_{50}$ [µM] | | | Phototoxicity Index, $PI^b$ | | MCR Index$^c$ |
|---|---|---|---|---|---|---|---|---|---|
| | HL60 | A549 | A549 spheroid | HL60 | A549 | A549 spheroid | HL60 | A549 | |
| Cisplatin | 3.1(+0.2) | 3.4(0.6) | n.d.$^d$ | 3.1(+0.1) | 3.5(+0.6) | 42(+3.6) | 1 | 1 | 12.4 |
| 3 | 81(+1.9) | 40(+4) | >300 | 240(+9) | 250(+5) | >300 | 3 | 6.3 | >7.5 |
| 4 | 1.6(+0.2) | 1.1(+0.3) | 21.3(+2.3) | >300 | 150(+7) | >300 | >188 | 136 | 19.4 |
| 5 | 2.6(+1.0) | 1.2(+0.1) | 64.6(+4.7) | 108(+1.9) | 250(+5) | >300 | 216 | 208 | 54 |
| ALA | 16.2(+3.2) | 21(+3.5) | >300 | >300 | 87.8(+5.5) | >300 | >18 | 4.2 | >14 | n.d. = not determined; see Dark $IC_{50}$ value.

Cell Survival Assay:

The HL60 promyelocytic leukemia cell line was obtained from ATCC and cultured in IMDM media (Invitrogen; Carlsbad, Calif.) supplemented with 10% serum supreme (Lonza; Basel, Switzerland) and penicillin/streptomycin at 37° C. with 5% $CO_2$. The A549 cell line was donated and cultured in DMEM supplemented with glutamax, 10% serum supreme, and penicillin/streptomycin at 37° C. with 5% $CO_2$. Cells were plated in Optimem (Life Technologies; Carlsbad, Calif.) supplemented with 1% serum supreme and penicillin/streptomycin at 30,000 cells per well in Costar 96 well flat bottom clear tissue culture treated plates for HL60 and 1500 cells/well for A549. The compounds were dosed from 0 to 300 µM, incubated with the cells for 12 hours, and then activated for 3 minutes with light using a 410 W projector fitted with a >450 nm cut-off filter. The cells were then incubated for 72 hours followed by the addition of Cell Titer Glo (Promega; Madison, Wis.) to determine viability. Dark controls were run in parallel. The resulting luminescence was measured using the SpectraFluor Plus Plate Reader (Tecan). Data were fit to an equation for a sigmoidal dose response using the equation below, where $y_i$ and $y_f$ are the initial and final signal intensities.

$$y = y_i + \frac{y_i - y_f}{1 + 10^{(logEC_{50}-x)Hillslope}}$$

Cell cytotoxicity studies were performed in HL60 leukemia cells and A549 lung cancer cells (see FIG. 7 and Table 3). Cells were incubated with compounds for 12 hours in the dark before irradiated with >450 nm light (410 W) for 3 minutes. Dark controls were run in parallel. Cell survival was quantified 72 hours later through the use of an ATP luciferase assay, and confirmed by Trypan Blue staining and manual counting. Cisplatin exhibited the same activity under light and dark conditions. Control compound 1, which causes single strand DNA breaks, exhibited only slightly enhanced activity upon irradiation. The light activated Ru(II) complexes caused near or complete cell death, which can be a challenge with light activated cytotoxic systems.

In Vivo Glutathione Assay:

A549 cells were plated in Optimem supplemented with 1% serum supreme and penicillin/streptomycin in 96 well plates as described above. The cells were allowed to adhere to the plate for 12 hours and then were dosed with glutathione from 0 to 16 mM, followed immediately by either cisplatin at the $IC_{100}$ or compound 4 at the $IC_{80}$ concentration. The $IC_{80}$ was chosen for compound 4 since glutathione did not show a cytoprotective effect in previous experiments with 4. Compound 4 was activated with 3 min of light as described above, and cytotoxicity measured 72 hours after compound activation and at the same time point for the dark samples. Cellular viability was determined by measuring ATP concentration with CellTiter Glo (Promega). Data were fit to an equation for sigmoidal dose response shown above using the Prism software package.

Tumor Spheroid Procedures:

A549 cells were seeded at 2,500 cells/well in 1.5% agarose coated 96-well plates. After 7 days the spheroids were dosed with compounds and incubated for 12 hrs. Following this, they were activated by light for 3 minutes using a 410 W projector fitted with a >450 nm cut-off filter, or kept in the dark. Cellular viability was determined 72 hours after light activation for the irradiated samples and at the same time point for the dark samples by measuring ATP concentration with CellTiter Glo (Promega). Data were fit to an equation for sigmoidal dose response shown above using the Prism software package.

3D tumor spheroids were used to test the compounds. Spheroids provide a system that approximates the complexity of in vivo tumors. These spheroids mimic the pathophysiology of tumors, including hypoxic/necrotic regions, changes in cell shape, high proportions of quiescent cells, alterations in gene expression profiles, and diminished permeability to drugs. Spheroids exhibited the phenomena of multicellular resistance (MCR), similar to the diminished efficacy of chemotherapeutics in vivo. To characterize the light-activated ruthenium compounds under more challenging and biologically relevant conditions, efficacy was assessed in a 3D tumor model by forming tumor spheroids with A549 cells.

Spheroids of about 600 μm in diameter were dosed with compounds and then either kept in the dark or irradiated with >450 nm light for 3 minutes. Significant light-selective cytoxicity was observed for 4, with an $IC_{50}$ value of 21 μM, while no cell death was observed up to 300 μM in the absence of light. Under the same conditions, the $IC_{50}$ for cisplatin fell to 42 μM in the spheroid model, and the PDT drug ALA (aminolevulinic acid) had no effect. The activity of 5 was lower than 4 in the spheroid, with a light-activated $IC_{50}$ of 64 μM.

Thus, the compounds exhibited twice the potency of cisplatin in both monolayer and tumor spheroids. The MCR index value is low for 4, similar to cisplatin (Table 3), which has a MCR lower than that of many other chemotherapeutics.

Example 3

This Example describes a novel ruthenium complex containing a dppz derivative that undergoes photochemical ligand substitution reactions in the presence of DNA. The compound exhibited selective photochemistry to generate a ligand-deficient and reactive metal center, along with a free coordinating ligand, in the presence of nucleic acids and organic solvents. The compound was sensitive to the DNA tertiary structure, displaying different reactivities in duplex and G-quadruplex DNA, providing a mechanism for the development of DNA structure-selective probes and effectors.

Chemicals used for synthesis were purchased from suppliers and used without further purification. Calf thymus (CT) DNA was purchased from Sigma-Aldrich, re-suspended in buffer (50 mM NaCl, 5 mM Tris buffer, pH 7.0) and sonicated (bath sonicator for 40 min followed by 10-15 1 sec pulses with a Branson Sonifier 250 (duty cycle=90% and output control=2; Danbury, Conn.) to provide shorter strands. The 15-mer oligonucleotide A was purchased from Integrated DNA Technologies (Coralville, Iowa) and the G-quadruplex sequence was purchased from Eurofins Scientific (Luxembourg), re-suspended, and annealed prior to use. The forward sequence for the 15-mer oligonucleotide A is 5'-CCT-CTC-TGG-TTC-TTC-3' and the reverse sequence is 5'-GAA-GAA-CCA-GAG-AGG-3'. The 15-mer oligonucleotide was re-suspended in $dH_2O$ and annealed by heating at 90° C. for 5 min then cooling slowly to ambient temperature and stored at −20° C. The G-quadruplex sequence is 5'-[AGGG $(TTAGGG)_3$]-3'. The G-quadruplex was re-suspended in buffer (10 mM potassium phosphate, 100 mM KCl, pH 7.0) and annealed by heating at 90° C. for 5 min then cooling slowly to ambient temperature, followed by incubation at 4° C. overnight, as previously reported.[1]

Figure 9A:
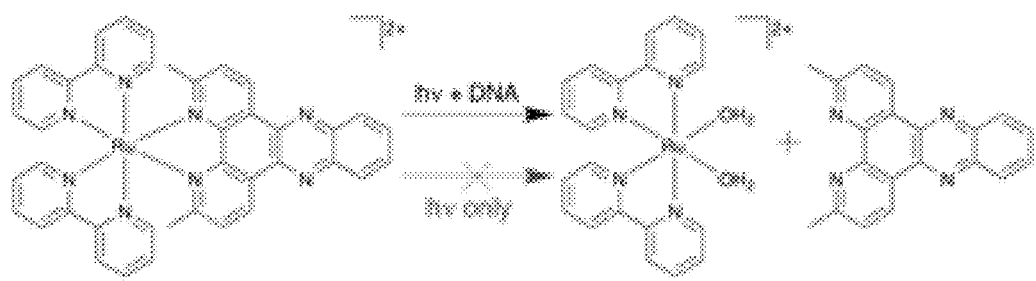
FIGS. 9A and 9B include (FIG. 9A) a scheme for the selective photoejection of dmdppz from 8 with λ>400 nm light, and (FIG. 9B) a chart of UV/Vis monitoring of photoejection in the presence of CT DNA (10:1 nucleotide: 8), where the kinetic fit for the photochemical reaction is shown in the inset.

Briefly, dipyrido[3.2-a:2',3'-c]phenazine (dppz) and $Ru(bpy)_2dppz$ (7) were prepared by known methods. To prepare 3,6-Dimethyl-dipyrido[3,2-a:2',3'-c]phenazine (dmdppz), dimethyl-dipyrido[3,2-a:2',3'-c]phenazine was first prepared by known methods modified to start with 2,9-dimethylphendione. Next, to prepare $Ru(bpy)_2dmdppz$ (8), $Ru(bpy)_2Cl_2.2H_2O$ (501 mg, 0.963 mmol) and 3,6-dimethyl-dipyrido[3,2-a:2',3'-c]phenazine (328 mg, 1.057 mmol) were added to 16 mL of degassed ethylene glycol in a 38 mL pressure tube. The mixture was heated at 150° C. with stirring and protected from light. After 16 hours the red solution was cooled to room temperature and poured into 50 mL of distilled water. Addition of a saturated aqueous $KPF_6$ solution produced a deep red precipitate that was collected by vacuum filtration and washed with $dH_2O$ (50 mL) and diethyl ether (50 mL). Purification of the solid was carried out by flash chromatography on $SiO_2$. Elution with saturated aq. $KNO_3/H_2O/CH_3CN$ (5/15/80) gave the pure complex. After column purification the complex as the $NO_3^-$ salt was dissolved in a minimal volume of water, and a saturated aq. solution of $KPF_6$ was added. The complex was extracted into $CH_2Cl_2$ and the solvent removed under reduced pressure to give a deep red solid. Thus, the light-switch $Ru(bpy)_2dppz$ (7) was transformed into a complex 8 probe that combines DNA sensing with ligand ejection photochemistry, as shown in FIG. 9, by strain-inducing methyl groups incorporated at the 3 and 6 positions of the dppz ligand (3,6-dimethyl dipyridylphenazine, dmdppz).

Compounds 7 and 8 were converted to the $Cl^-$ salt prior to procedures. The $PF_6^-$ salt of each complex was dissolved in a minimal volume of acetone (1-2 mL), followed by the addition of a solution of t-butyl ammonium chloride (1 g dissolved in 5 mL of acetone) producing a precipitate that was filtered through glass wool, washed with acetone (50 mL) and eluted with acetonitrile. The solvent was removed under reduced pressure to give the pure complex.

To perform crystallography, all crystal manipulations requiring exposure to light were conducted as rapidly as possible. To this end, the crystal(s) were plunged directly into liquid nitrogen and mounted using cryo-tongs. Single crystals of compounds 7 and 8 were grown by slow evaporation of methylene chloride in diethyl ether, mounted in inert oil and transferred to the cold gas stream of the diffractometer. X-ray diffraction data were collected at 90.0(2) K on a Bruker-Nonius X8 Proteum diffractometer with graded-multilayer focused $CuK(\alpha)$ x-rays. Raw data were integrated, scaled, merged and corrected for Lorentz-polarization effects using the APEX2 package. Corrections for absorption were applied using SADABS and XABS2. The structure was solved by direct methods (SHELXS-97) and difference Fourier (SHELXL-97). Refinement was carried out against $F^2$ by weighted full-matrix least-squares (SHELXL-97), and assessed with the aid of an R-tensor. Hydrogen atoms were found in difference maps but subsequently placed at calculated positions and refined using a riding model. Non-hydrogen atoms were refined with anisotropic displacement parameters. Atomic scattering factors were taken from the International Tables for Crystallography.

Figure 10:
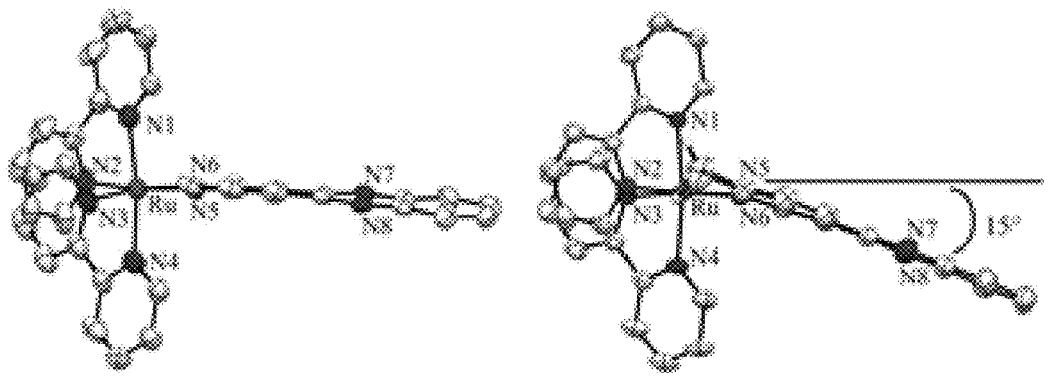
FIG. 10 includes images showing the crystal structure of racemic (left) compound 7 and (right) compound 8, where ellipsoids are drawn to 50% probability and hydrogen atoms are excluded for clarity.

The crystal structures of racemic $Ru(bpy)_2dppz$ (7) and $Ru(bpy)_2dmdppz$ (8) confirmed that addition of the methyl groups induced distortion about the metal center (FIG. 10). The Ru—N bonds were lengthened in the strained ligand, with an average of 2.10 Å for the Ru—N bonds in dmdppz, in contrast to 2.07 Å for dppz. The main distortion in compound 8 is a 15° bending of the dmdppz ligand from the normal plane of the octahedral complex, due to the clash of the methyl group with the auxiliary ligands. The bpy ligands in either compound did not experience significant distortions.

Figure 9B:
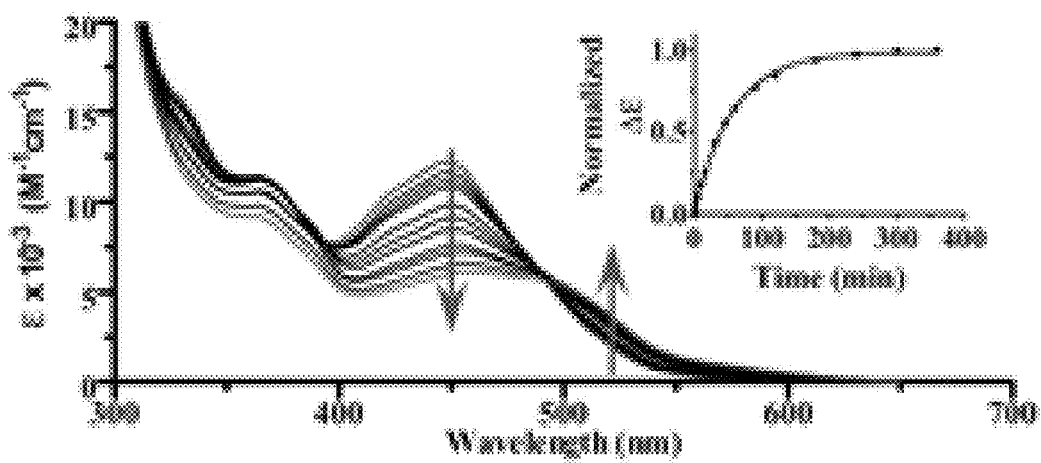

Complex 8 was rather unreactive in water, exhibiting slow photodecomposition when exposed to visible light ($\lambda$>400 nm; $t_{1/2}$>8 hours), suggesting a more discerning switch that could exploit triggers with light. The photoreactivity was increased by more than an order of magnitude in the presence of duplex DNA oligonucleotides and calf thymus (CT) DNA, with $t_{1/2}$ values of 31-41 minutes, as shown in Table 4. The photoejection process was characterized by both a red shift in the absorption spectra and decreased extinction coefficient. Ligand ejection was selective, as indicated by the presence of isosbestic points in the UV/Vis spectra taken as a function of irradiation time (FIG. 9B). It appeared that only the dmdppz ligand was ejected, and the photoreaction led to covalent metalation of the DNA.

TABLE 4

Photophysical and photochemical properties for 7 and 8 for various reaction conditions.

| Experimental Conditions[a] | $\lambda_{max}$ (nm) (7) | Half-life (minutes) (8) |
|---|---|---|
| $H_2O$ | — | >480 |
| $D_2O$ | 605 (weak) | 140 ± 10 |
| $CH_2Cl_2$ | 596 | 0.5 ± 0.05 |
| DMF | 638 | 25 ± 2 |
| CT DNA | 619 | 41 ± 2 |
| 15 mer oligonucleotide A | 615 | 31 ± 0.5 |
| G-Quadruplex | 613 | 13.5 ± 1 |
| BSA | — | 146 ± 8 |

The distortion of compound 8 did not appear to significantly affect the DNA binding affinity, as similar $K_b$ values of $1 \times 10^7$ and $3 \times 10^7$ $M^{-1}$ were determined for racemic mixtures of 7 and 8 with CT DNA. Intercalation of both complexes was consistent with the reduced mobility of supercoiled plasmid DNA in agarose gels, and the modulation of the absorption spectra in the presence of DNA, characterized by hypochromism of both the $\pi$-$\pi$* of the dppz ligand and the MLCT transitions, with maximal effect at a ratio of 2:1 DNA base pairs to metal center. Thus, the strained complex retained DNA-sensing capabilities of other $Ru^{II}$ "light-switch" molecules and photochemical reactivity.

Alternative tertiary structures of DNA provide potential for greater selectivity in gene and cellular regulation than double stranded motifs, and G-quadruplex structures are medically relevant targets for cancer research and therapies. Complex 8 was tested as a photochemical probe for the telomeric G-quadruplex structure using the sequence [AGGG(TTAGGG)$_3$]. Upon binding the quadruplex, the photoejection rate for 8 increased 3-fold compared to standard double helix CT DNA, giving a $t_{1/2}$ of 13.5 minutes.

The selectivity of the probe for DNA was compared to protein by testing the ejection with bovine serum albumin (BSA). There was no observable emission for 7 in the presence of BSA, and 8 appeared to photodecompose, with no isobestic points in the absorption spectra and a $t_{1/2}$ of 146 minutes. The reactivity with a hydrophobic protein is similar to the behavior in water.

The photochemical behaviour of 8 paralleled the photophysical characteristics of unstrained $Ru^{II}$ complexes containing the dppz ligand. For example, the emission intensity of 7 and other dppz complexes as well as of 8 increased in nonpolar, aprotic solvents ($t_{1/2}$>8 hrs in water, $t_{1/2}$=0.5 min in $CH_2Cl_2$). The luminescence of $Ru^{II}$ dppz complexes was greater in $D_2O$ than $H_2O$; and the ejection of 8 showed a similar isotope effect of >3.4.

Figure 11:
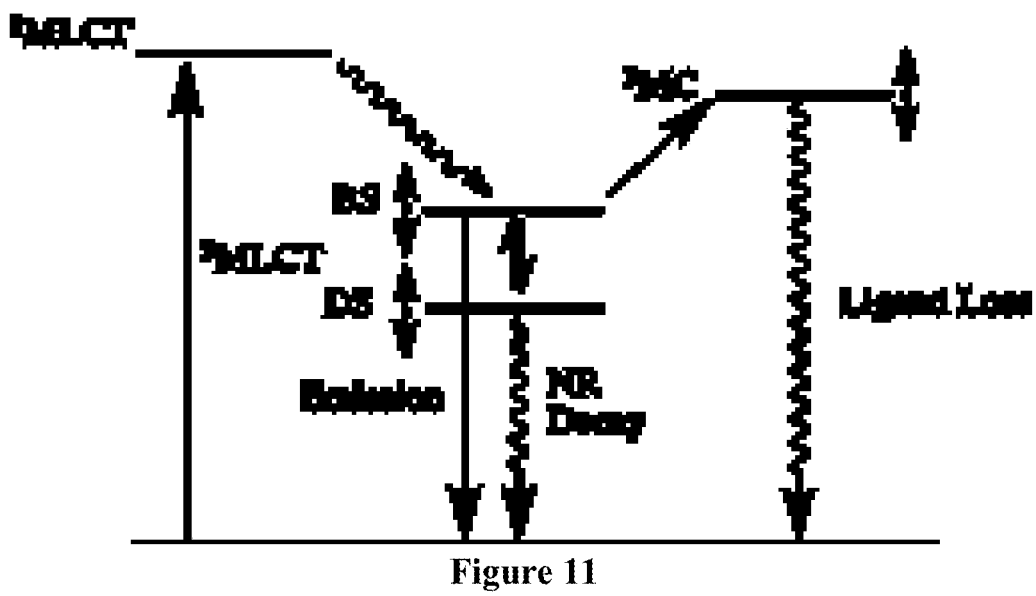
FIG. 11 includes an illustration showing a Jablonski diagram for compound 8 (BS=Bright State; DS=Dark State; NR Decay=nonradiative decay).

A proposed Jablonski diagram in FIG. 11 illustrates the interplay between different states. The "bright" and "dark" states are in thermal equilibrium as a function of the environment, and the dissociative $^3$MC state can be accessed only from the "bright" state. Population of the "dark" state is enhanced in solvents such as water, and results in alternative non-radiative decay pathways that reduce the yield of photoejection. Without being bound by theory, the data suggests that the complex 8 undergoes ligand ejection photochemistry efficiently under conditions that destabilize polar charge transfer states and reduce population of the "dark" state MLCT and it associated non-radiative decay pathways.

The present ruthenium complex therefore act as a dual photochemical DNA sensor and metalating agent. Strain is beneficial to induce photoejection, but environmental factors may also affect other nonradiative decay processes.

Example 4

This Example compares the synthesis and characterization of exemplary Ru(II) complexes having positive and negative overall charges. The compounds include Ru(bathophenanthroline)$_3$ (9), which is hydrophobic with a high DNA binding affinity, and Ru(bathophenanthorlinedisulfonate)$_3$ (10), which is hydrophilic with a high affinity for proteins. Both complexes are efficient singlet oxygen ($^1O_2$) generators with the same quantum yields for $^1O_2$ production ($\Phi_A$) and similar molar extinction coefficients (E). Compound 9 carries a +2 overall charge while 10 has a −4 overall charge.

Table 5 provides a summary of physical and photophysical characteristics of the two complexes. This Example shows that the compounds have differences in potency, cellular uptake, localization, and mechanism of cytotoxicity. This Example also shows that negatively and positively charged Ru(III) complexes can be compatible as PDT agents.

TABLE 5

Physical and Photophysical Properties of 9 and 10

| Property | Compound 9 | Compound 10 |
|---|---|---|
| Charge | +2 | −4 |
| Log P | 1.8 ± 0.02 | −2.2 ± 0.12 |
| $\lambda_{max}$ (nm) | 460 | 462 |
| $\epsilon$ ($M^{-1}$ $cm^{-1}$) | 29,500 | 29,300 |
| $\lambda_{em}$ (nm) | 632 | 632 |
| $\Phi_{PL}$ | 0.101 | 0.176 |
| $\Phi_A$ | 0.42 | 0.43 |

DNA Damage and Cytotoxicity

As both 9 and 10 are efficient catalysts for the light-activated generation of $^1O_2$ ($\Phi_A$=0.42, 0.42). Their DNA damaging properties were assessed with pUC19 plasmid DNA using gel electrophoresis. Serial dilutions of the compounds (0-500 µM) were mixed with 40 µg/mL pUC19 plasmid DNA in 10 mM potassium phosphate buffer (pH 7.4) protected from light or irradiated with a 200 W light source for total light doses of 40 J/cm² blue filtered light (>400 nm). Samples were then incubated for 24 hours at room temperature protected from light. Controls were prepared to simulate single and double strand DNA breaks, and the DNA samples resolved on agarose gels.

Samples were resolved using 1% agarose gels prepared in tris-acetate (TA) buffer. Each lane was loaded with 0.3 µg of pUC19 and the samples run for 90 minutes at 100 mV. The gels were stained with 500 ng/mL ethidium bromide in TA buffer at room temperature for 40 minutes. The gels were subsequently washed with fresh TA buffer at room temperature for 40 min then imaged using a ChemiDoc™ MP System from Bio-Rad.

Figure 12A:
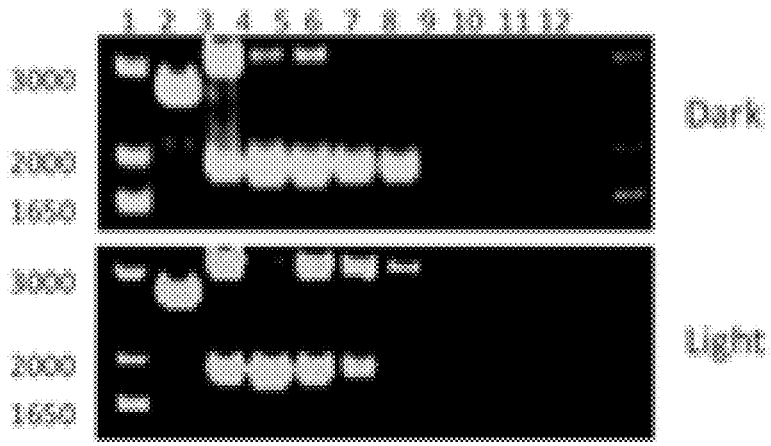
FIGS. 12A to 12D includes images showing agarose gel electrophoresis of 40 μg/ml pUC19 with increasing concentrations of (FIG. 12A) 9 and (FIG. 12B) 10 in the dark or irradiated (lanes 1 and 12, DNA molecular weight standard; lane 2, linear (reaction with EcoR1); lane 3, relaxed circle (reaction with $Cu(phen)_2$); lanes 4-11, 0, 7.5, 15, 30, 60, 120, 240, and 500 μM compound); and further includes charts showing the cytotoxicity dose response of (FIG. 12C) 1 and (FIG. 12D) 10 in the dark (open squares) or irradiated (closed circles).
Figure 12B:
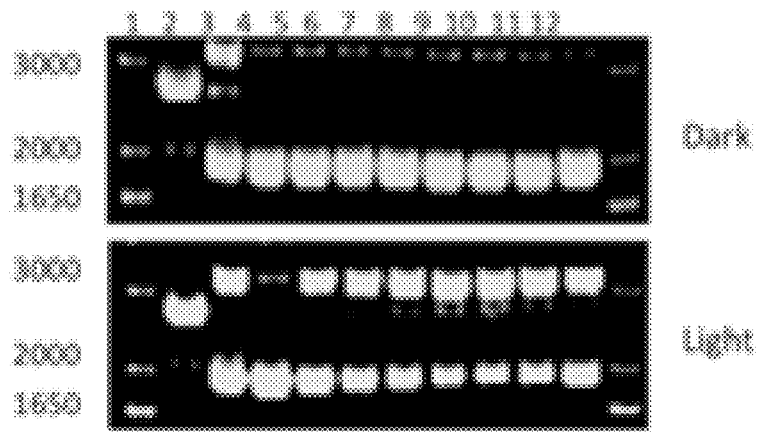
Figure 12C:
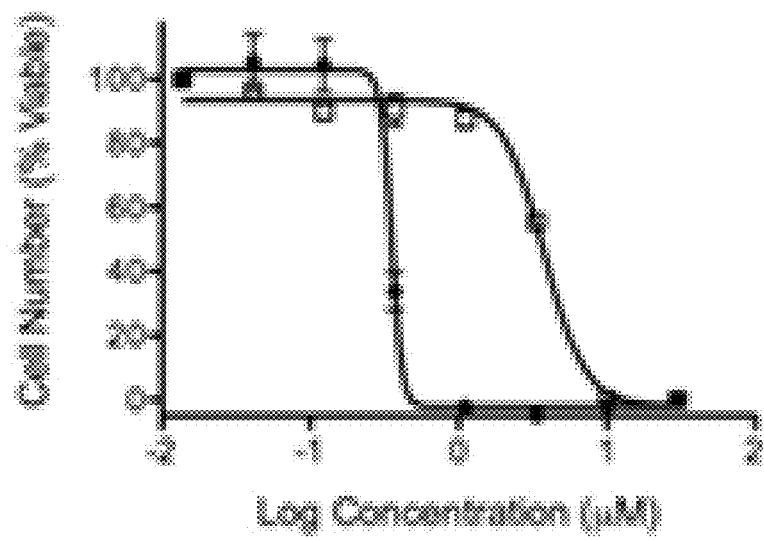
Figure 12D:
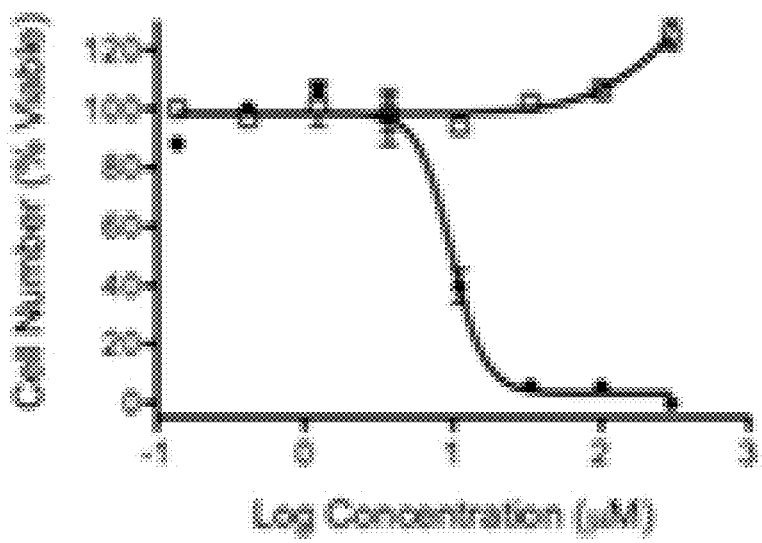

Compound 9 binds strongly with DNA, and precipitation of the complex with the DNA was observed at concentrations above 31.3 µM both in the light and in the dark (FIG. 12A). In contrast, 10 is a more hydrophilic molecule, and the negatively charged sulfonate functional groups were anticipated to cause electrostatic repulsions between the complex and the negatively charged backbone of the DNA. DNA precipitation or smearing was not observed with up to 500 µM of 2 (FIG. 12B). However, when exposed to light both 9 and 10 induced single strand DNA breaks, creating relaxed circular plasmid. However, for 10, the amount of relaxed plasmid did not exhibit any concentration dependence above 125 µM, suggesting either a reduction in $\Phi_A$ as the concentration of the complex is increased, or alternative quenching mechanisms that impede DNA damage.

As both compounds are capable of light-induced DNA damage, the cytotoxicity of 1 and 2 were evaluated in the A549 human non-small cell lung cancer, the HL60 human promyelocytic leukemia, and the Jurkat human T lymphoblastoid cell lines in presence and absence of 3 J/cm$^2$ of >400 nm light. A549 cells were grown in 75 cm$^2$ culture flasks in DMEM supplemented with 10% FBS and 1% pen-strep (DMEM) at 37° C., 5% CO$_2$. Cell media was replaced twice a week and cells were maintained below 70% confluence. HL60 cells were grown in 75 cm$^2$ culture flasks in IMDM supplemented with 10% FBS and 1% pen-strep (IMDM) at 37° C., 5% CO$_2$. HL60 cells were diluted 1:5 once a week with IMDM to maintain a cell concentration below 2×10$^6$ cells/mL.

The IC$_{50}$ values across the cell lines for 1 ranged from 0.62 to 3.75 µM in the dark. In the presence of light, potency was increased to a range of 0.075 to 0.35 µM, resulting in an average phototoxicity index (PI=IC$_{50}$ (dark)/IC$_{50}$ light) of 10- to 20-fold (FIG. 12, Table 5).

The high toxicity of 9 in the absence of light is in marked contrast to the behavior of 2, where no toxicity was observed in the dark at concentrations up to 300 µM across all cell lines. Compound 10 was effective in killing cells only when irradiated, with IC$_{50}$ values ranging from 3.3 to 17.25 µM, consistent with the concentrations required for in vitro DNA damage. This provides for a large therapeutic window, as cell death was not observed for samples in the absence of irradiation.

Compound 9 was toxic to cells upon irradiation and induced cell death more rapidly than traditional DNA damaging agents such as cisplatin. Upon treatment with 9 and irradiation, cell death was observed within 2 hours. Cell death was slower for the samples kept in the dark, with approximately 30% viable cells remaining at 24 hours. For compound 10 70% of viable cells remained at 24 hours and 55% remained at 48 hours after irradiation. The disparity in the potencies, therapeutic windows, and rates of cell killing for the two compounds and similar ability to sensitize $^1$O$_2$ suggested that they were acting through different cellular mechanisms.

Cellular Uptake and Subcellular Localization

Both 9 and 10 were emissive, allowing for direct visualization of their cellular uptake and localization. Flow cytometry and fluorescence microscopy were used to provide relative uptake values, the time dependence of compound uptake, and information on the subcellular localization of the compounds. 9 was assayed at 5 µM while 20 µM of 10 was assayed. Flow cytometry with HL60 cells revealed greater uptake of 9 compared with 10 at time points of 2 and 24 hours, with an 11.6-fold increase and 8.2-fold increase in signal respectively. Between the time points of 2 and 24 hours, the average emission of cells incubated with 9 increased by 2.8-fold while the amount of 10 increased by 4-fold. This data was supported by direct quantification of the number of ruthenium atoms per cell using Inductively Coupled Plasma Optical Emission Spectroscopy (ICP-OES). The relative amount of compound 9 in cells versus the cell media increased approximately 4-fold from 2 to 24 hours, from 5.6% to 22%. Less of compound 10 entered the cells, with a maximal percentage uptake of 0.7% at 24 hours. This degree of uptake is comparable to cisplatin dosed at the same concentration (20 µM, 0.8% at 24 hours). Irradiation increased the amount of 10 within the cells to 1.6%. Complete cell death was observed with 9 within 2 hours of light exposure.

The emission of 9 and 10 was measured in A549 cells using an Apoptome microscope. The relative rates of uptake of each of the complexes were analyzed as a function of time, and both 9 and 10 were visible inside cells as early as 2 hours after compound addition, consistent with the flow data and the ICP-OES results. Images were taken at 2, 8, 18 and 24 hours, and intracellular levels of both complexes appeared to plateau around 8 hours. The uptake data showed good agreement between the three techniques and two cell lines, suggesting similar behavior in adherent and suspension cell lines.

Figure 13A:
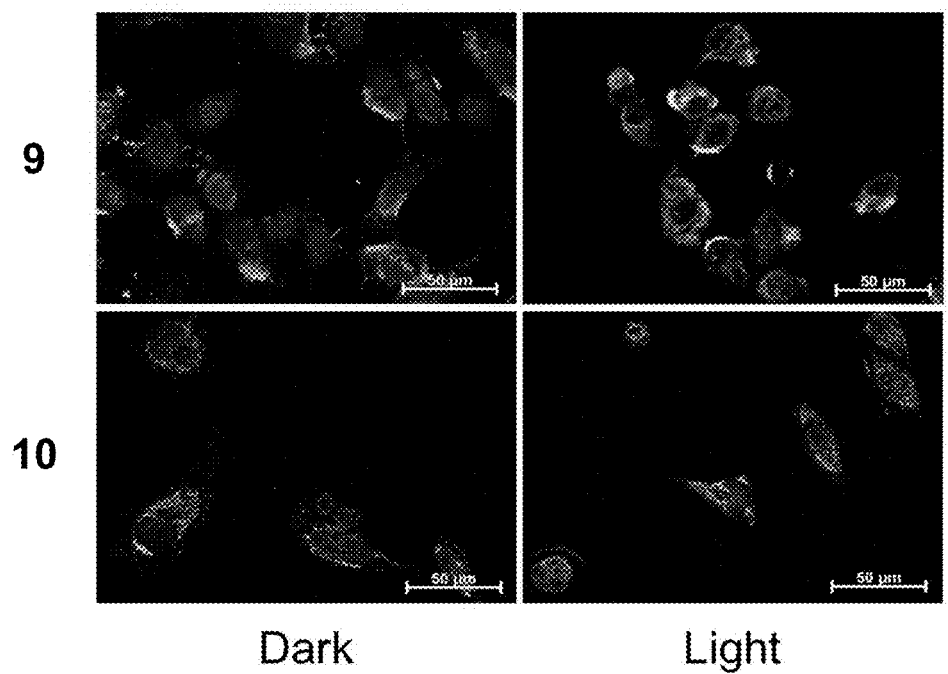
FIGS. 13A and 13B includes apoptome micrographs showing subcellular localization of 9 and 10 at 8 hours, where (FIG. 13A) Mitotracker Green FM was used to image mitochondria, and (FIG. 13B) Lysotracker Green DND-26 was used to image lysosomes.
Figure 13B:
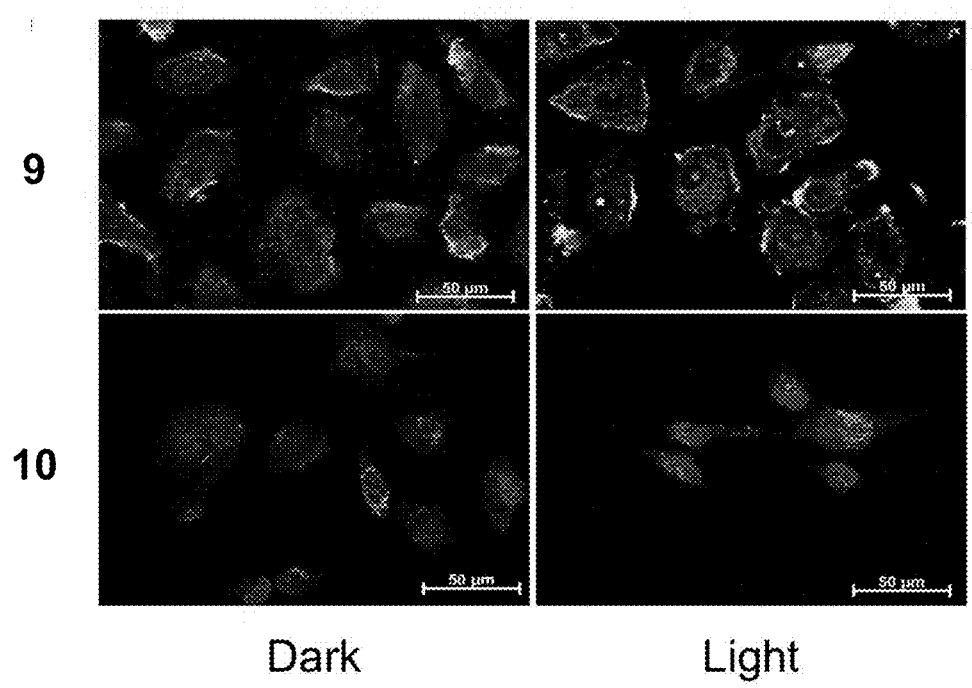

Differences in the intracellular localization of 9 and 10 were evaluated by determining colocalization of luminescence of the compound and fluorescent markers of organelles in A549 cells. Overlap in signals between the compounds, cellular nucleus, mitochondria and lysosome was measured over a 24 hour period. FIG. 13 shows the 8 hour time point, which demonstrates that 9 and 10 have different localization profiles. Compound 9 substantially localized to lysosomes and the mitochondria in the absence of light, while 10 remained primarily in the cytosol. Exposure to light did have some impact on compound localization, where 9 induced nuclear localization of the mitochondrial and lysosome markers (FIGS. 13A and 13B), suggesting that photo-induced damage mediated by 9 reduced the integrity of the nuclear membrane. 10 was primarily observed in lysosomes after irradiation, and did not co-localize with mitochondria (FIGS. 13A and 13B). In addition, irradiation in the presence of 10 did not result in the appearance of organelle markers in the nucleus, suggesting the nuclear membrane remained intact. Neither 9 nor 10 was found to associate with the cell membrane or membranes of organelles.

Mitochondrial Function and Time Dependence for Cell Death

Figure 14A:
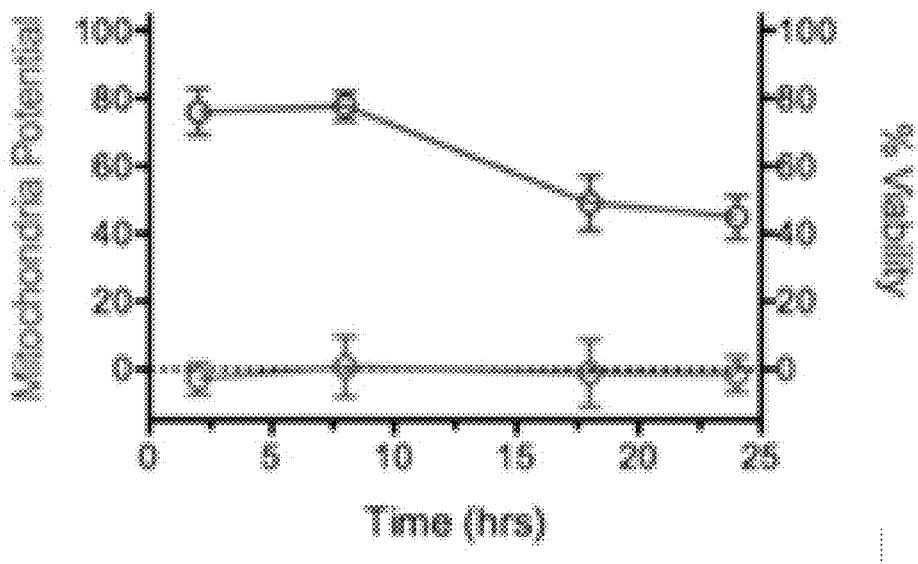
FIGS. 14A to 14D includes charts showing mitochondrial potential and cell viability of HL60 cells as a function of time for (FIG. 14A) 9, dark, (FIG. 14B) 9, irradiated.
Figure 14B:
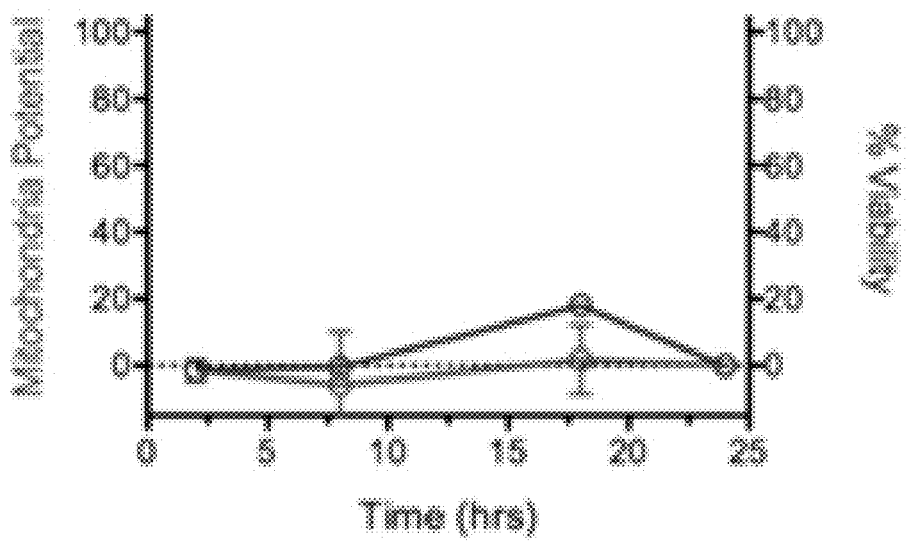
Figure 14C:
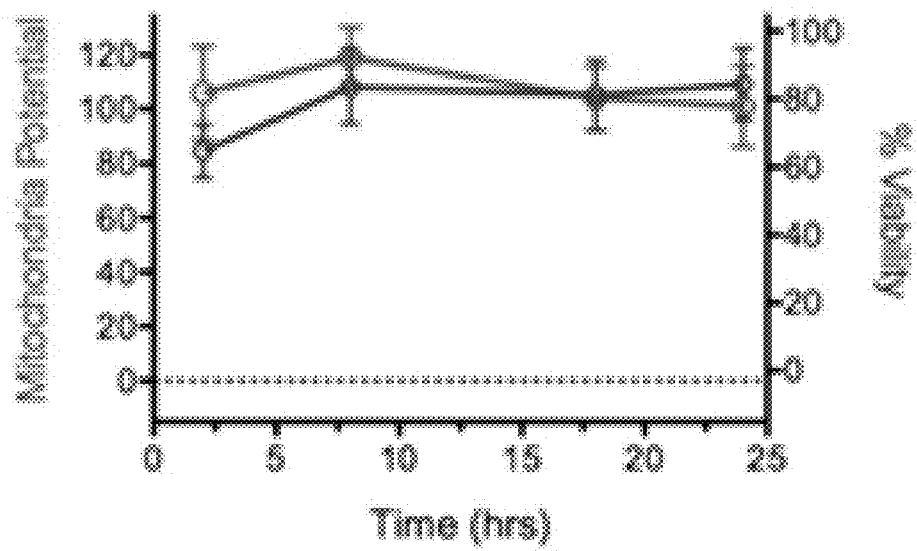

Without being bound by theory, compound 9 localized within mitochondria, which may account for its toxicity in the absence of irradiation. To determine if the interactions of either 9 or 10 with the mitochondria resulted in reduced mitochondrial function, mitochondrial membrane potential was measured using tetramethylrhodamine ethyl ester (TMRE). TMRE is a cationic dye that accumulates in active motochondria as a result of the negative membrane potential (Δψm). Inactive or depolarized mitochondria exhibit a decreased membrane potential and TMRE does not localize in these organelles. Compound 9 induced rapid and complete depolarization of mitochondria both in the dark and upon irradiation (FIGS. 14A and 14B).

Cell viability did not parallel mitochondrial potential. Mitochondrial function was completely impaired at 2 hours post treatment with 9 in the dark, viability decreased slowly, with 44±6% viable cells remaining after 24 hours. In contrast, both mitochondrial function and cell viability fell to about 0% within 2 hours of irradiation. Thus, while 9 impedes mitochondrial function within 2 hours even in the absence of light, irradiation induced additional damage that resulted in cell death along with the loss of mitochondrial function.

Figure 14D:
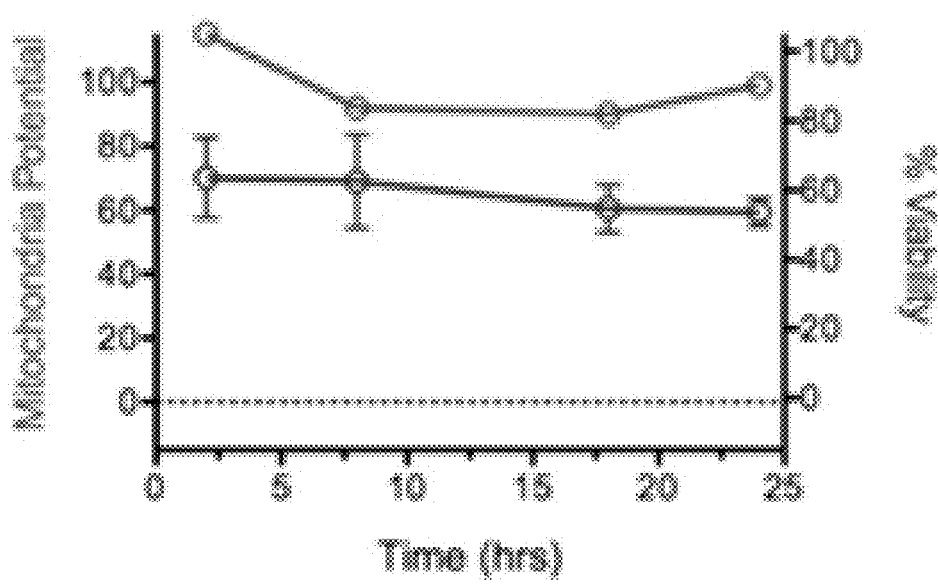

Compound 10 did not significantly reduce the mitochondrial potential either when irradiated or in the dark over a 24 hour period. Irradiation did reduce cell viability to 70±12% at 2 hours and 59±4% after 24 hours, but this occurred without a significant decrease in the relative mitochondrial potential (FIG. 14D), indicating 10 did not act through inhibition of mitochondrial function. This suggests that rapid mitochondria failure may be connected to the dark toxicity of 9, and the lack of mitochondrial localization and inhibition be connected to the limited dark toxicity of 10.

The disconnect between the mitochondrial potential and cell viability for compound 9 in the dark may also indicate that disruption of mitochondrial activity does not lead to immediate cell death.

Mechanism of Cell Death

Figure 15A:
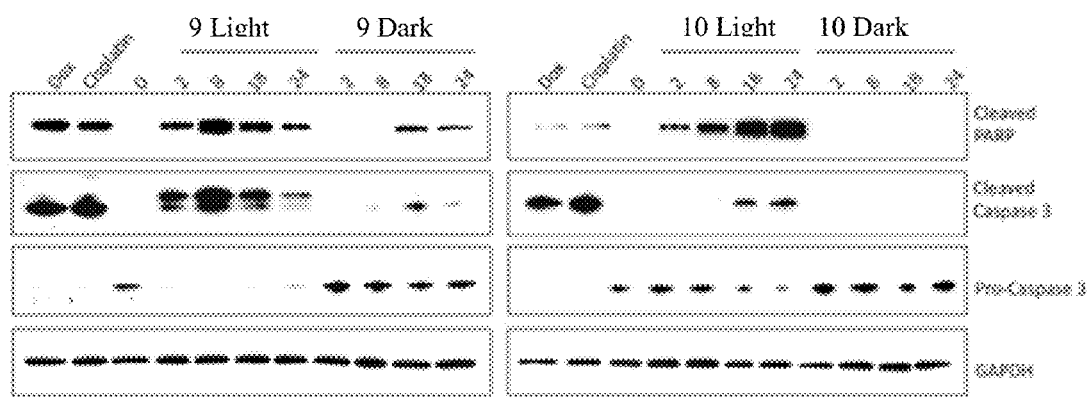
FIGS. 15A and 15B include images of (FIG. 15A) a Western blot analysis of cleaved PARP, Caspase 3, and Pro-Caspase 3, where GAPDH was used as a loading control, and (FIG. 15B) agarose gel electrophoresis of genomic DNA harvested from HL60 cells after treatment with various agents (Lanes 1 and 9; ladder; 2, no compound control; 3, 10% EtOH, 24 hours (necrosis control); 4, cisplatin, 24 hours (apoptosis control); 5, 9+hv, 8 hours; 6, 9−hv, 8 hours; 7, 10+hv, 24 hours; 8, 10−hv, 24 hours).
Figure 15B:
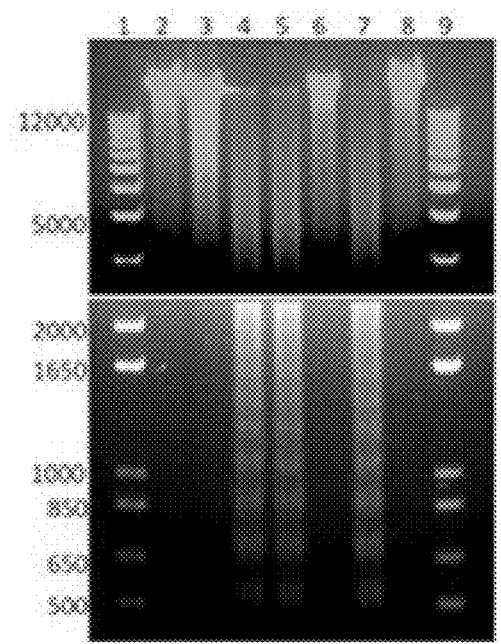

Given the different cellular localization properties and time profiles for cell death induced by 9 and 10, the mechanism of cell death was investigated. Indicators of apoptotic cell death (activation of PARP and caspase 3 through proteolysis) were determined in HL60 cells treated with either 9 or 10 (FIGS. 15A and 15B). The known apoptotic inducing compounds, cisplatin and doxorubicin, were run in parallel. Compound 9 induced the proteolytic activation of both PARP and caspase 3 within 2 hours of irradiation and was maximal after 8 hours (FIG. 15). In the absence of light, PARP and caspase 3 were observed with 9, but after 18 and 24 hours and to a lesser degree. In the absence of irradiation the amount of inactive procaspase 3 did not change.

Exposure of 10 to light induced PARP as early as 2 hours, and increasing amounts of PARP were observed over the course of 24 hours (FIG. 15). The increase in the level of activated caspase 3 occurred on a slower time scale than PARP cleavage, with the protein observed at 18 and 24 hrs. Thus, the irradiated samples may possibly undergo apoptosis that is not primarily signaled through caspase 3. Cells treated with 10 and protected from light did not display PARP or caspase 3 cleavage, indicating limited cytotoxicity in the absence of light. The level of procaspase 3 did not change over 24 hours.

Since 10 showed PARP induction without significant caspase 3 activation, as compared to 9 and cisplatin or doxorubicin, a mechanism of cell death through necrosis was explored. The generation of an alternate 55 kDa PARP fragment was determined by immunoblot as a marker for necrosis with 10% (v/v) ethanol used as a control that induces necrosis. Exposure of HL60 cells to 9 produced this fragment at significant levels both when protected from light and when irradiated, consistent with necrosis. Cisplatin and doxorubicin also produced this cleavage product, indicating that some cells had progressed into necrosis. In contrast, cells exposed to 10 both in the presence and absence of irradiation produced a lower level of the 55 kDa PARP fragment, similar to the untreated cells, suggesting necrosis was not a significant cell death pathway for this compound.

To further analyze the mechanisms of cell death induced by 9 and 10, the degradation pattern of genomic DNA was investigated. DNA laddering was observed as a result of DNA fragmentation stemming from the execution phase of apoptosis. In contrast, necrotic cell death lacked this characteristic laddering effect, allowing differentiation between these two mechanisms. H L60 cells were exposed to the Ru(II) complexes, cisplatin, and 10% ethanol, followed by genomic DNA isolation and resolution by gel electrophoresis. The apoptosis inducer, cisplatin, initiated DNA fragmentation resulting in a laddering pattern on the gel (FIG. 15B). This laddering was absent in the cells treated with ethanol and compounds 9 and 10 in the dark. However, both compounds 9 and 10 displayed similar laddering patterns as cisplatin when irradiated, suggesting apoptosis is a major cell-death pathway for both compounds when irradiated. In contrast, given the cytotoxicity of 9 in the dark and the presence of the 55 kDa PARP fragment, it appears that necrotic cell death is one pathway for 1. For compound 10 the absence of DNA laddering may be a result of the lack of cytotoxicity of the negatively charged compound.

Thus, ligand modifications of the present complexes can provide compounds with divergent physical properties and biological activities. Compound 9, having high DNA affinity, localized to the mitochondria and induced rapid membrane depolarization and necrotic cell death. Compound 10, with an overall −4 charge, was taken up into cancer cells to a sufficient degree to mediate light-induced cell death through an apoptotic pathway.

Example 5

This Example describes additional specific embodiments the presently-disclosed subject matter. The structure, light $IC_{50}$, dark $IC_{50}$, and phototoxicity index (i.e., dark $IC_{50}$/light $IC_{50}$) for each compound is given below. The methods for making and characterizing the compounds are based on the methodologies described in the previous examples.

TABLE 6

Physical and Photophysical Properties Exemplary Compounds

| Structure | Light $IC_{50}$ (µM) | Dark $IC_{50}$ (µM) | Phototoxicity Index |
|---|---|---|---|
| Cisplatin | 3.1 | 3.1 | 1 |
| Ru(bpy)$_2$-6,6'dmbpy | 1.5 | 300 | 200 |
| Ru(bpy)$_2$dmdpq | 0.6 | 250 | 400 |
| Ru(bpy)$_2$dmphen | 0.4 | 8 | 20 |
| Ru(bpy)$_2$dmdppz | 14 | 65 | 4.6 |
| Ru(bpy)$_2$bathocuprione | 3.3 | 27 | 8.18 |
| Ru(dmphen)$_2$bpy | 1.2 | 150 | 125 |
| Ru(dmphen)$_2$bathophen | 1.7 | 4.5 | 2.5 |
| Ru(dmphen)$_2$dpq | 0.22 | 250 | 1,130 |
| Ru(dmphen)$_2$dppz | 0.5 | 150 | 300 |
| Ru(dmphen)$_2$phen | 0.14 | 35 | 250 |

Bpy = 2,2'-bipyridine
Phen = 1,10-phenanthroline
Dmphen = 2,9-Dimethyl-1,10-phenanthroline
6,6'-dmbpy = 6,6'-dimethyl, 2,2'-bipyridine
dpq = dipyrido[3,2-f:2',3'-h]-quinoxaline
dppz = dipyrido[3,2-a:2',3'-c]phenazine
dmdpq = 2,9-dimethyl dpq
dmdppz = 2,9-dimethyl dppz
bathophen = bathophenanthroline While the following terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a compound" includes a plurality of such compounds, and so forth.

Unless otherwise indicated, all numbers expressing quantities, properties, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

REFERENCES

Throughout this document, various references are mentioned. All such references, including those listed below, are incorporated herein by reference.
1. Garas, A. M. S.; Vagg, R. S., Synthesis of some novel derivatives of 1,10-phenanthroline. *J. Heterocycl. Chem.* 2000, 37 (1), 151-158.
2. Caspar, J. V.; Meyer, T. J., Photochemistry of MLCT Excited-States—Effect of Nonchromophoric Ligand Variations on Photophysical Properties in the Series Cis-Ru(Bpy)$_2$L$_2^{2+}$. *Inorg Chem* 1983, 22 (17), 2444-2453.
3. Keck, M. V., DNA topology analysis in the undergraduate biochemistry laboratory. *J. Chem. Educ.* 2000, 77 (11), 1471-1473.
4. Thederahn, T. B.; Kuwabara, M. D.; Larsen, T. A.; Sigman, D. S., Nuclease Activity of 1,10-Phenanthroline Copper—Kinetic Mechanism. *J. Am. Chem. Soc.* 1989, 111 (13), 4941-4946.
5. Vrouenraets, M. B.; Visser, G. W.; Snow, G. B.; van Dongen, G. A., *Anticancer Res.* 2003, 23 (1B), 505-22.
6. Dolmans, D. E.; Fukumura, D.; Jain, R. K., *Nat. Rev. Cancer* 2003, 3 (5), 380-7.
7. Cepeda, V.; Fuertes, M. A.; Castilla, J.; Alonso, C.; Quevedo, C.; Perez, J. M., *Anticancer Agents Med. Chem.* 2007, 7 (1), 3-18.
8. Farrer, N. J.; Woods, J. A.; Salassa, L.; Zhao, Y.; Robinson, K. S.; Clarkson, G.; Mackay, F. S.; Sadler, P. J., *Angew. Chem. Int. Ed. Engi.* 2010, 49 (47), 8905-8.
9. Mackay, F. S.; Woods, J. A.; Heringova, P.; Kasparkova, J.; Pizarro, A. M.; Moggach, S. A.; Parsons, S.; Brabec, V.; Sadler, P. J., *Proc. Nat. Acad. Sci. U.S.A* 2007, 104 (52), 20743-20748.
10. Singh, T. N.; Turro, C., *Inorg. Chem.* 2004, 43 (23), 7260-7262.
11. Monro, S.; Scott, J.; Chouai, A.; Lincoln, R.; Zong, R.; Thummel, R. P.; McFarland, S. A., *Inorg. Chem.* 2010, 49 (6), 2889-900.
12. Mahnken, R. E.; Billadeau, M. A.; Nikonowicz, E. P.; Morrison, H., *J. Am. Chem. Soc.* 1992, 114 (24), 9253-9265.
13. Lutterman, D. A.; Fu, P. K. L.; Turro, C., *J. Am. Chem. Soc.* 2006, 128 (3), 738-739.
14. Wang, J.; Higgins, S. L. H.; Winkel, B. S. J.; Brewer, K. J., *Chem. Commun.* 2011, 47 (35), 9786-9788.
15. Higgins, S. L.; Tucker, A. J.; Winkel, B. S. J.; Brewer, K. J., *Chem. Commun.* 2012, 48 (1), 67-9.
16. Juris, A.; Balzani, V.; Barigelletti, F.; Campagna, S.; Belser, P.; Vonzelewsky, A., *Coord. Chem. Rev.* 1988, 84, 85-277.
17. Van Houten, J., Watts, R. J., *J. Am. Chem. Soc.* 1976, 98 (16), 4853-58.
18. Durham, B.; Caspar, J. V.; Nagle, J. K.; Meyer, T. J., *J. Am. Chem. Soc.* 1982, 104 (18), 4803-4810.
19. Ford, P. C., *Coord. Chem. Rev.* 1982, 44 (1), 61-82.
20. Durham, B.; Walsh, J. L.; Carter, C. L.; Meyer, T. J., *Inorg. Chem.* 1980, 19 (4), 860-865
21. Baranoff, E.; Barigelletti, F.; Bonnet, S.; Collin, J. P.; Flamigni, L.; Mobian, P.; Sauvage, J. P., *Photofunctional Transition Metals Complexes* 2007, 123, 41-78.
22. Mobian, P.; Kern, J. M.; Sauvage, J. P. *Angew. Chem. Int. Ed. Engl.* 2004, 43 (18), 2392-95
23. Collin, J. P.; Jouvenot, D.; Koizumi, M.; Sauvage, J. P., *Inorg. Chem.* 2005, 44 (13), 4693-4698.
24. Lincoln, P.; Norden, B., *J. Phys. Chem. B* 1998, 102 (47), 9583-9594.
25. Greguric, I.; Aldrich-Wright, J. R.; Collins, J. G., *J. Am. Chem. Soc.* 1997, 119 (15), 3621-3622.
26. Collins, J. G.; Sleeman, A. D.; Aldrich-Wright, J. R.; Greguric, I.; Hambley, T. W., *Inorg. Chem.* 1998, 37 (13), 3133-3141.
27. Collins, J. G.; Aldrich-Wright, J. R.; Greguric, I. D.; Pellegrini, P. A., *Inorg. Chem.* 1999, 38 (24), 5502-5509.
28. Tachiyashiki, S.; Ikezawa, H.; Mizumachi, K., *Inorg. Chem.* 1994, 33 (4), 623-625.
29. Laemmel, A. C.; Collin, J. P.; Sauvage, J. P., *Eur. J. Inorg. Chem.* 1999, (3), 383-386.
30. Keck, M. V.; Lippard, S. J., *J. Am. Chem. Soc.* 1992, 114 (9), 3386-3390.
31. Demeunynck, M., Bailly, C., Wilson, W. D., *Small Molecule DNA and RNA Binders: From Synthesis to Nucleic Acid Complexes*. Wiley-VCH: New York, 2003.
33. Abbott, A., *Nature* 2003, 424 (6951), 870-2.
34. Friedrich, J.; Seidel, C.; Ebner, R.; Kunz-Schughart, L. A., *Nat. Protoc.* 2009, 4 (3), 309-24.
35. Kunz-Schughart, L. A.; Freyer, J. P.; Hofstaedter, F.; Ebner, R., *J. Biomol. Screen* 2004, 9 (4), 273-85.
36. Herrmann, R.; Fayad, W.; Schwarz, S.; Berndtsson, M.; Linder, S., *J. Biomol. Screen* 2008, 13 (1), 1-8.
37. Desoize, B.; Jardillier, J., *Crit Rev. Oncol. Hematol.* 2000, 36 (2-3), 193-207.
38. Farrer, N. J.; Salassa, L.; Sadler, P. J., *Dalton Trans.* 2009, (48), 10690-701.
39. Fleisher, M. B.; Waterman, K. C.; Turro, N. J.; Barton, J. K., *Inorg. Chem.* 1986, 25 (20), 3349-3351.
40. Mei, H. Y.; Barton, J. K., *Proc. Natl. Acad. Sci. U.S.A.* 1988, 85 (5), 1339-43.
41. Janaratne, T. K.; Yadav, A.; Ongeri, F.; MacDonnell, F. M., *Inorg. Chem.* 2007, 46 (9), 3420-2.
42. Sun, Y.; Joyce, L. E.; Dickson, N. M.; Turro, C., *Chem. Commun.* 2010, 46 (36), 6759-61
43. Boca, S. C.; Four, M.; Bonne, A.; van der Sanden, B.; Astilean, S.; Baldeck, P. L.; Lemercier, G., *Chem. Commun.* 2009, (30), 4590-2.
44. Barigelletti, F.; Juris, A.; Balzani, V.; Belser, P.; Von Zelewsky, A., *Inorg. Chem.* 1983, 22 (22), 3335-3339.
45. Baranoff, E.; Collin, J. P.; Furusho, Y.; Laemmel, A. C.; Sauvage, J. P., *Chem. Commun.* 2000, (19), 1935-1936.
46. Baranoff, E.; Collin, J. P.; Furusho, J.; Furusho, Y.; Laemmel, A. C.; Sauvage, J. P., *Inorg. Chem.* 2002, 41 (5), 1215-1222.
47. Caldecott, K. W., *Nat. Rev. Genet.* 2008, 9 (8), 619-31.
48. A. E. Friedman, J.-C. Chambron, J.-P. Sauvage, N. J. Turro and J. K. Barton, *J. Am. Chem. Soc.,* 1990, 112, 4960.
49. Y. Jenkins, A. E. Friedman, N. J. Turro and J. K. Barton, *Biochemistry,* 1992, 31, 10809.

50. A. W. McKinley, P. Lincoln and E. M. Tuite, *Coord. Chem. Rev.*, 2011, 255, 2676.
51. Y. Sun, D. A. Lutterman and C. Turro, *Inorg. Chem*, 2008, 47, 6427; (b) Y. Sun and C. Turro, *Inorg. Chem.*, 2010, 49, 5025; (c) C. Kuhnt, M. Karnahl, S. Tschierlei, K. Griebenow, M. Schmitt, B. Schäfer, S. Krieck, H. Görls, S. Rau, B. Dietzek and J. Popp, *Phys Chem Chem Phys*, 2010, 12, 1357; (d) M. Schwalbe, M. Karnahl, S. Tschierlei, U. Uhlemann, M. Schmitt, B. Dietzek, J. Popp, R. Groake, J. G. Vos and S. Rau, *Dalton Trans.*, 2010, 39, 2768; (e) A. J. McConnell, M. H. Lim, E. D. Olmon, H. Song, E. E. Dervan and J. K. Barton, *Inorg. Chem.*, 2012, 51, 12511; (f) M. R. Gill, J. Garcia-Lara, S. J. Foster, C. Smythe, G. Battaglia and J. A. Thomas, *Nat. Chem.*, 2009, 1, 662; (g) M. R. Gill, H. Derrat, C. G. W. Smythe, G. Battaglia and J. A. Thomas, *Chembiochem*, 2011, 12, 877.
52. (a) W. Chen, C. Turro, L. A. Friedman, J. K. Barton and N. J. Turro, *J. Phys. Chem. B*, 1997, 101, 6995; (b) E. J. C. Olson, D. Hu, A. Hörmann, A. M. Jonkman, M. R. Arkin, E. D. A. Stemp, J. K. Barton and P. F. Barbara, *J. Am. Chem. Soc.*, 1997, 119, 11458; (c) M. K. Brennaman, T. J. Meyer and J. M. Papanikolas, *J. Phys. Chem. A*, 2004, 108, 9938.
53. M. G. Walker, V. Gonzalez, E. Chekmeneva and J. A. Thomas, *Angew. Chem. Int. Ed.*, 2012, 51, 12107.
54. (a) M. H. Lim, H. Song, E. D. Olmon, E. E. Dervan and J. K. Barton, *Inorg. Chem.*, 2009, 48, 5392; (b) H. Song, J. T. Kaiser and J. K. Barton, *Nat. Chem.*, 2012, 4, 615.
55. A. W. McKinley, P. Lincoln and E. M. Tuite, *Dalton Trans.*, 2013, 42, 4081.
56. B. S. Howerton, D. K. Heidary and E. C. Glazer, *J. Am. Chem. Soc.*, 2012, 134, 8324.
57. E. Wachter, D. K. Heidary, B. S. Howerton, S. Parkin and E. C. Glazer, *Chem. Commun.*, 2012, 48, 9649.
58. P. S. Wagenknecht and P. C. Ford, *Coord. Chem. Rev.*, 2011, 255, 591.
59. (a) E. Baranoff, J.-P. Collin, J. Furusho, Y. Furusho, A.-C. Laemmel and J.-P. Sauvage, *Inorg. Chem.*, 2002, 41, 1215; (a) A.-C. Laemmel, J.-P. Collin and J.-P. Sauvage, *Eur. J. Inorg. Chem.*, 1999, 383.
60. (a) M. T. Ashby, *J. Am. Chem. Soc.*, 1995, 117, 2000; (b) M. T. Ashby, S. S. Alguindigue, J. D. Schwane and T. A. Daniel, *Inorg. Chem.*, 2001, 40, 6643.
61. B. S. Howerton, E. Wachter, D. K. Heidary, S. Parkin and E. C. Glazer, manuscript in preparation.
62. For Ru(phen)$_2$dppz, $K_b$>10$^8$ M$^{-1}$ has been reported; see (a) C. Hiort, P. Lincoln and B. Norden, *J. Am. Chem. Soc.*, 1993, 115, 3448; (b) S. R. Dalton, S. Glazier, B. Leung, S. Win, C. Megatulski and S. J. N. Burgmayer, *J. Biol. Inorg. Chem.*, 2008, 13, 1133. A similar result with $K_b$>10$^6$ M$^{-1}$ was reported in Ref. 1 and other publications.
63. Decreases in hypochromicity have been rationalized as indicative of reduced insertion into the DNA π-stack due to steric clash; see J.-G. Liu, Q.-L. Zhang, X.-F. Shi, L.-N. Ji, *Inorg. Chem.* 2001, 40, 5045.
64. S. Burge, G. N. Parkinson, P. Hazel, A. K. Todd and S. Neidle, *Nucleic Acids Res.*, 2006, 34, 5402.
65. H. Han and L. H. Hurley, *Trends Pharmacol. Sci.*, 2000, 21, 136-142.
66. S. Shi, X. Geng, J. Zhao, T. Yao, C. Wang, D. Yang, L. Zheng and L. Ji, *Biochimie*, 2010, 92, 370.
67. U. Kragh-Hansen, *Pharmacol. Rev.*, 1981, 33, 17.
68. R. B. Nair, B. M. Cullum and C. J. Murphy, *Inorg. Chem.*, 1997, 36, 962.
69. M. K. Brennaman, J. H. Alstrum-Acevedo, C. N. Fleming, P. Jang, T. J. Meyer and J. M. Papanikolas, *J. Am. Chem. Soc.*, 2002, 124, 15094.
70. C. Reichardt, *Chem. Rev.*, 1994, 94, 2319.
71. B. Lippert, ed., *Cisplatin: Chemistry and Biochemistry of a Leading Anticancer Drug*, Wiley-VCH, 1999.
72. S. M. Cohen and S. J. Lippard, *Progress in Nucleic Acid Research and Molecular Biology*, Vol 67, 2001, 67, 93-130.
73. N. S. Hadjiliadis, E., ed., *Metal complex-DNA interactions*, Wiley, 2009.
74. C. Moucheron, *New J. Chem.*, 2009, 33, 235-245.
75. L. J. K. Boerner and J. M. Zaleski, *Curr. Opin. Chem. Biol.*, 2005, 9, 135-144.
76. B. M. Zeglis, V. C. Pierre and J. K. Barton, *Chem Commun (Camb)*, 2007, 4565-4579.
77. M. R. Gill and J. A. Thomas, *Chem Soc Rev*, 2012, 41, 3179-3192.
78. F. R. Svensson, J. Andersson, H. L. Amand and P. Lincoln, *J Biol Inorg Chem*, 2012, 17, 565-571.
79. O. Zava, S. M. Zakeeruddin, C. Danelon, H. Vogel, M. Gratzel and P. J. Dyson, *Chembiochem*, 2009, 10, 1796-1800.
80. C. A. Puckett and J. K. Barton, *J Am Chem Soc*, 2007, 129, 46-47.
81. C. A. Puckett and J. K. Barton, *Biochemistry*, 2008, 47, 11711-11716.
82. C. A. Puckett and J. K. Barton, *J Am Chem Soc*, 2009, 131, 8738-8739.
83. C. A. Puckett and J. K. Barton, *Bioorg Med Chem*, 2010, 18, 3564-3569.
84. C. A. Puckett, R. J. Ernst and J. K. Barton, *Dalton Trans*, 2010, 39, 1159-1170.
85. J. K. Barton, L. A. Basile, A. Danishefsky and A. Alexandrescu, *Proceedings of the National Academy of Sciences of the United States of America-Biological Sciences*, 1984, 81, 1961-1965.
86. B. M. Goldstein, J. K. Barton and H. M. Berman, *Inorg. Chem.*, 1986, 25, 842-847.
87. T. Rabilloud, J. M. Strub, S. Luche, A. van Dorsselaer and J. Lunardi, *Proteomics*, 2001, 1, 699-704.
88. F. N. Castellano and J. R. Lakowicz, *Photochem Photobiol*, 1998, 67, 179-183.
89. A. Lamanda, A. Zahn, D. Roder and H. Langen, *Proteomics*, 2004, 4, 599-608.
90. D. Garcia-Fresnadillo, Y. Georgiadou, G. Orellana, A. M. Braun and E. Oliveros, *Helv. Chim. Acta*, 1996, 79, 1222-1238.
91. A. E. Friedman, C. V. Kumar, N. J. Turro and J. K. Barton, *Nucleic Acids Res.*, 1991, 19, 2595-2602.
92. S. Zanarini, L. Della Ciana, M. Marcaccio, E. Marzocchi, F. Paolucci and L. Prodi, *J Phys Chem B*, 2008, 112, 10188-10193.
93. A. Hergueta-Bravo, M. E. Jimenez-Hernandez, F. Montero, E. Oliveros and G. Orellana, *J. Phys. Chem. B*, 2002, 106, 4010-4017.
94. S. Gobeil, C. C. Boucher, D. Nadeau and G. G. Poirier, *Cell Death and Differentiation*, 2001, 8, 588-594.
95. J. Q. Wang, P. Y. Zhang, C. Qian, X. J. Hou, L. N. Ji and H. Chao, *J Biol Inorg Chem*, 2014, 19, 335-348.
96. T. F. Chen, W. J. Mei, Y. S. Wong, J. Liu, Y. N. Liu, H. S. Xie and W. J. Zheng, *Medchemcomm*, 2010, 1, 73-75.
97. T. Chen, Y. Liu, W. J. Zheng, J. Liu and Y. S. Wong, *Inorg Chem*, 2010, 49, 6366-6368.
98. T. Joshi, V. Pierroz, S. Ferrari and G. Gasser, *ChemMedChem*, 2014.
99. D. Garcia-Fresnadillo and G. Orellana, *Helv Chim Acta*, 2001, 84, 2708-2730.

What is claimed is:

1. A compound of the following formula:

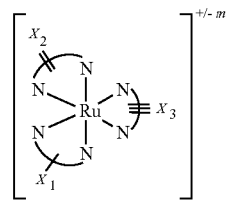

wherein:
ligands $X_1$, $X_2$, and $X_3$, the same or different from one another, are selected from bidentate nitrogen heterocycles, optionally substituted with one or more of alkyl, aryl, amine, C(O), C(O)R, S, S(R), O, O(R), amide, $SR_4$, $PR_4$, $OR_4$, halogen, $SO_3H$, alkylamino and P, wherein R is selected from H, OH, alkyl, and aryl;
m is −6 to +6; and
at least one of the ligands $X_1$, $X_2$, and $X_3$ is a strain-inducing ligand and are released when the compound is exposed to light, wherein the ligands X1, X2, and X3 are selected from pyridyls, phenanthrolines, quinolines, 6 membered heteroaryl rings containing one nitrogen atom, or a combination thereof, and are optionally fused to a 6-membered carbocyclic ring or 6 membered heteroaryl ring containing 1 or 2 nitrogen atoms, and are optionally substituted with one or more of alkyl, aryl, amine, C(O), C(O)R, S, S(R), O, O(R), amide, $SR_4$, $PR_4$, $OR_4$, halogen, $SO_3H$, alkylamino and P, wherein R is selected from H, OH, alkyl, and aryl; or
a pharmaceutically acceptable derivative thereof.

2. The compound of claim 1, wherein at least one of $X_1$, $X_2$, and $X_3$ is a strain-inducing ligand having bond lengths and/or bond angles that deviate by 5% or more relative to the ideal bond lengths and/or bond angles determined by VSEPR.

3. The compound of claim 1, wherein at least one of $X_1$, $X_2$, and $X_3$ are selected from polypyridyl.

4. The compound of claim 1, wherein at least one of $X_1$, $X_2$, and $X_3$ are selected from:

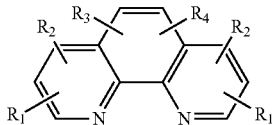

wherein
each $R_1$ is independently selected from H, amine, amide, alkyl, aryl, $SR_4$, $PR_4$, O, $OR_4$, halogen, or $SO_3H$, $R_4$ being H, alkyl, or aryl, or wherein $R_1$ and $R_3$ taken together with the carbon atoms to which they are bonded, form a substituted or unsubstituted ring containing about 4-6 ring carbon atoms that optionally include one or more N;
each $R_2$ is H, amine, amide, alkyl, aryl, $SR_4$, $PR_4$, O, $OR_4$, halogen, or $SO_3H$;
each $R_3$ is independently selected from H, amine, amide, alkyl, aryl, $SR_4$, $PR_4$, O, $OR_4$, halogen, or $SO_3H$, or wherein $R_3$ and $R_4$ taken together with the carbon atoms to which they are bonded, form a substituted or unsubstituted ring containing about 4-6 ring carbon atoms that optionally include one or more N; and
each $R_4$ is H, amine, amide, alkyl, aryl, $SR_4$, $PR_4$, O, $OR_4$, halogen, or $SO_3H$.

5. The compound of claim 1, wherein at least one of $X_1$, $X_2$, and $X_3$ are selected from:

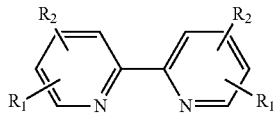

wherein
each $R_1$ is independently selected from H, amine, amide, alkyl, aryl, $SR_4$, $PR_4$, O, $OR_4$, halogen, or $SO_3H$, $R_4$ being H, alkyl, or aryl, or wherein $R_1$ and $R_3$ taken together with the carbon atoms to which they are bonded, form a substituted or unsubstituted ring containing about 4-6 ring carbon atoms that optionally include one or more N; and
each $R_2$ is H, amine, amide, alkyl, aryl, $SR_4$, $PR_4$, O, $OR_4$, halogen, or $SO_3H$.

6. The compound of claim 1, wherein at least one of $X_1$, $X_2$, and $X_3$ are selected from:

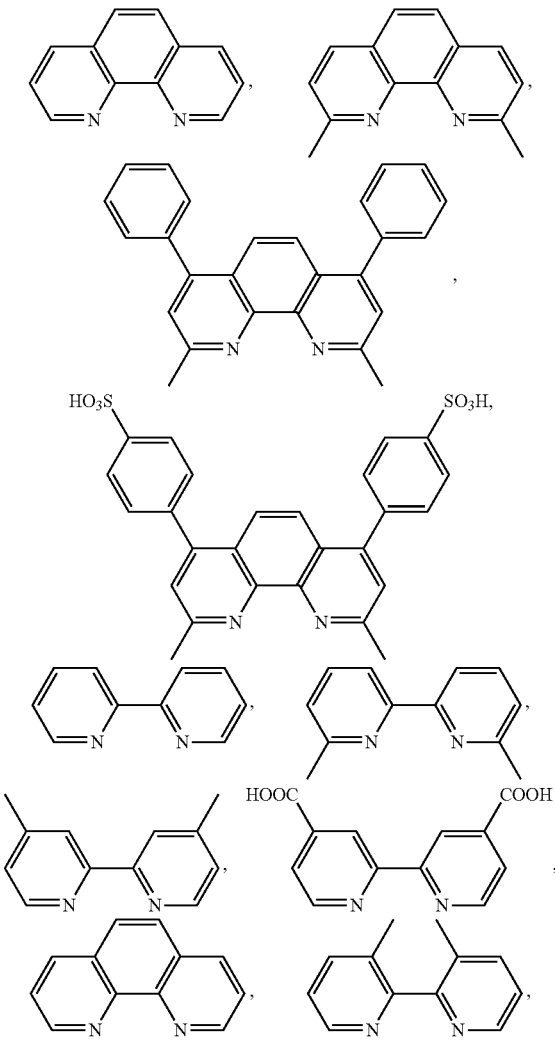

41
-continued
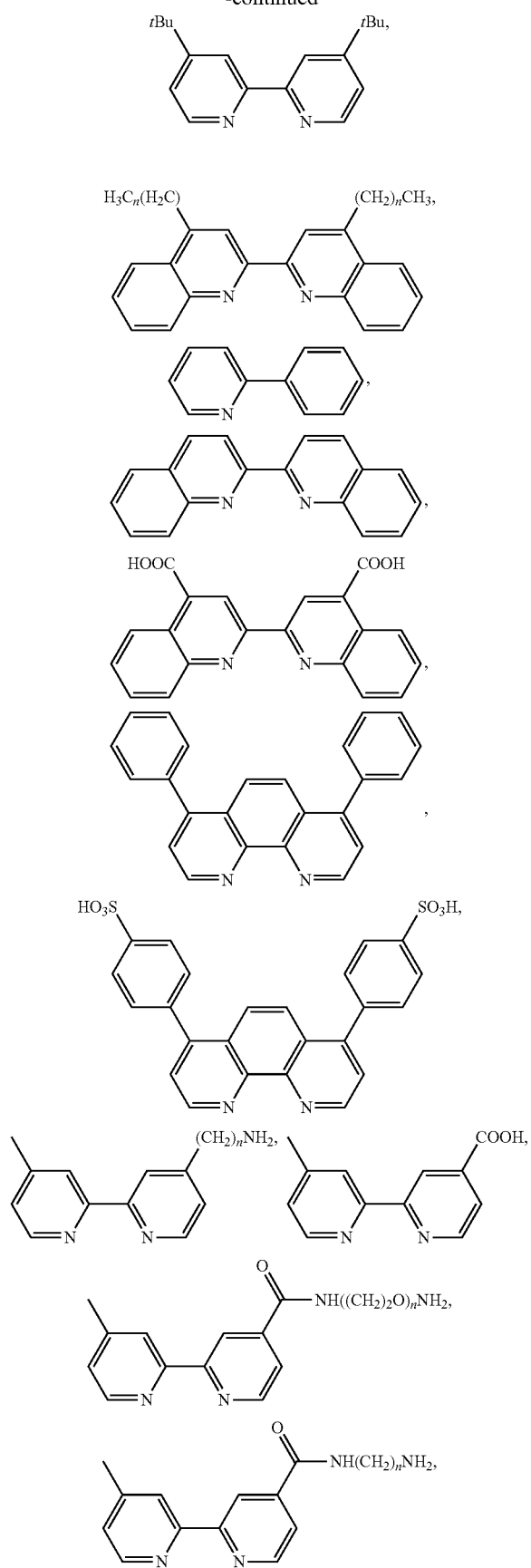
42
-continued
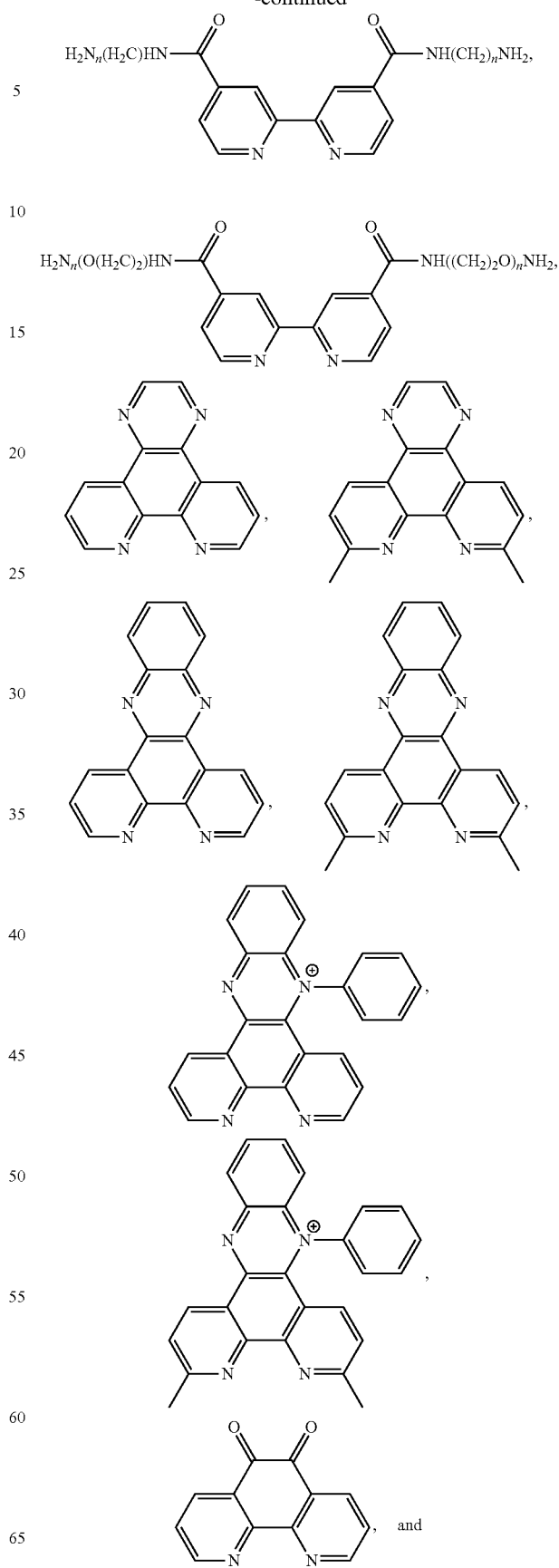

-continued

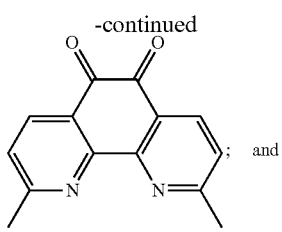
; and wherein when the at least one of $X_1$, $X_2$, and $X_3$ is

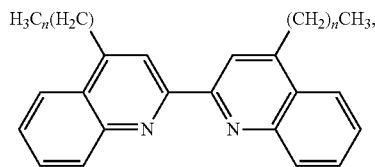

n is from 1 to 16,
when the at least one of $X_1$, $X_2$, and $X_3$ is

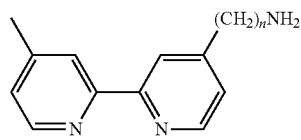

n is 5, 7, or 9;
when the at least one of $X_1$, $X_2$, and $X_3$ is

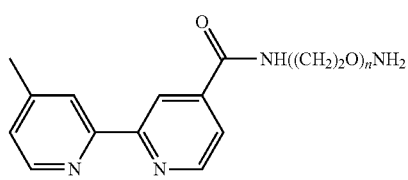

n is 2 or 4;
when the at least one of $X_1$, $X_2$, and $X_3$ is

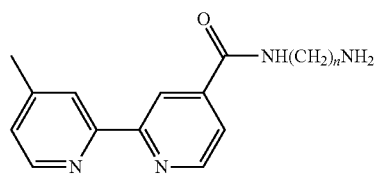

n is 4 or 8;
when the at least one of $X_1$, $X_2$, and $X_3$ is

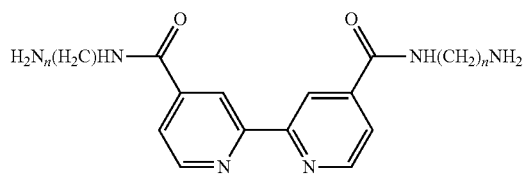

n is 4 or 8; and when the at least one of $X_1$, $X_2$, and $X_3$ is

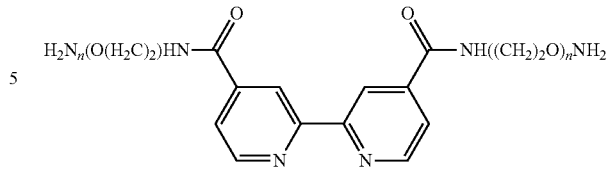

n is 2 or 4.

7. The compound of claim 1, wherein at least one of $X_1$, $X_2$, and $X_3$ are a methylated bidentate nitrogen heterocycle.

8. The compound of claim 1, according to the formula:

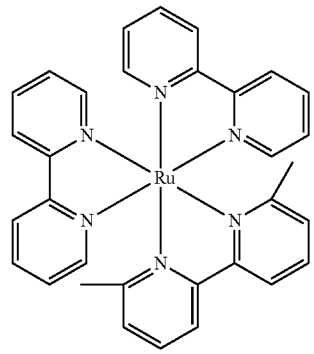

9. The compound of claim 1, according to the formula:

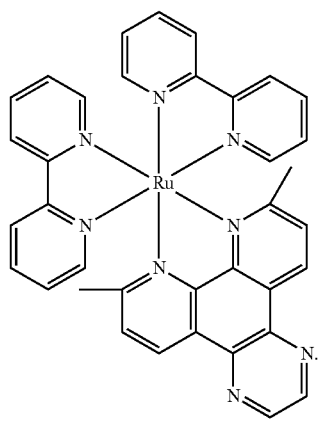

10. The compound of claim 1, according to the formula:

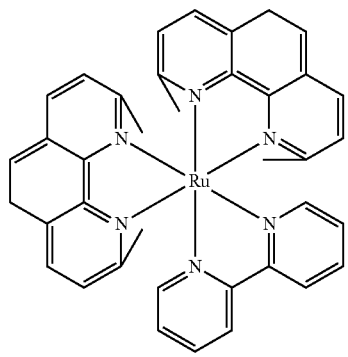

11. The compound of claim 1, according to the formula:

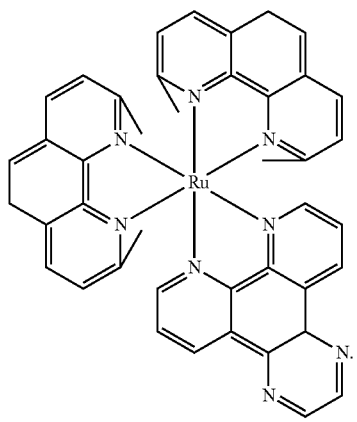

12. The compound of claim 1, according to the formula:

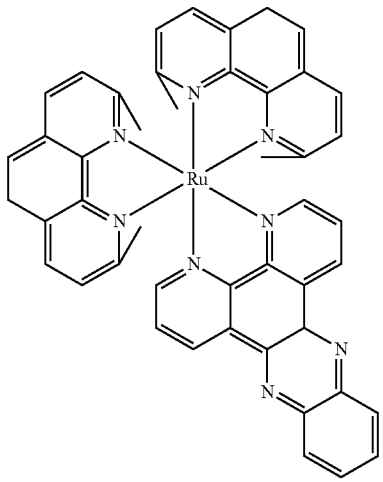

13. The compound of claim 1, according to the formula:

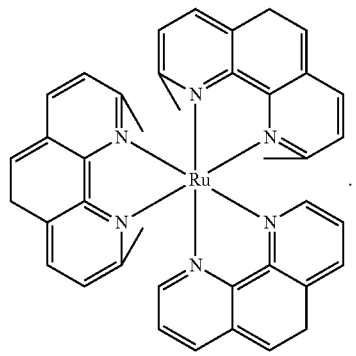

14. The compound of claim 1, further comprising a targeting agent.

15. The compound of claim 14, wherein the targeting agent selected from folate, estrogen, and erlotinib.

16. The compound of claim 1, wherein at least one of the ligands is a therapeutic agent.

17. The compound of claim 16, wherein the therapeutic agent is hydroxyquinoline.

18. The compound of claim 1, wherein the light includes a wavelength of about 500 nm to about 1000 nm.

19. The compound of claim 1, wherein m is less than zero.

20. A pharmaceutical composition, comprising a compound of the following formula:

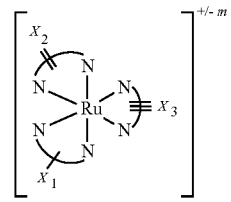

wherein:
ligands $X_1$, $X_2$, and $X_3$, the same or different from one another, are selected from bidentate nitrogen heterocycles, or a combination thereof and are optionally substituted with one or more of alkyl, aryl, amine, C(O), C(O)R, S, S(R), O, O(R), amide, $SR_4$, $PR_4$, $OR_4$, halogen, $SO_3H$, alkylamino and P, wherein R is selected from H, OH, alkyl, and aryl; and
m is −6 to +6; and
at least one of the ligands $X_1$, $X_2$, and $X_3$ is a strain-inducing ligand and are released when the compound is exposed to light, wherein the ligands X1, X2, and X3 are selected from pyridyls, phenanthrolines, quinolines, 6 membered heteroaryl rings containing one nitrogen atom, or a combination thereof, and are optionally fused to a 6-membered carbocyclic ring or 6 membered heteroaryl ring containing 1 or 2 nitrogen atoms, and are optionally substituted with one or more of alkyl, aryl, amine, C(O), C(O)R, S, S(R), O, O(R), amide, $SR_4$, $PR_4$, $OR_4$, halogen, $SO_3H$, alkylamino and R, wherein R is selected from H, OH, alkyl, and aryl; or
a pharmaceutically acceptable derivative thereof; and
a pharmaceutically-acceptable carrier.

21. A method of treating lung cancer or leukemia in a subject, comprising:
administering an effective amount of the compound to the subject, the compound including the following formula:

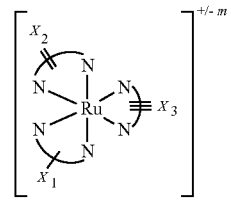

wherein:
$X_1$, $X_2$, and $X_3$, the same or different from one another, are selected from bidentate nitrogen heterocycles, and
m is −6 to +6; and
at least one of the ligands $X_1$, $X_2$, and $X_3$ is a strain-inducing ligand and are released when the compound is exposed to light, wherein the ligands X1, X2, and X3 are selected from pyridyls, phenanthrolines, quinolines, 6 membered heteroaryl rings containing one nitrogen atom, or a combination thereof, and are optionally fused to a 6-membered carbocyclic ring or 6 membered heteroaryl ring containing 1 or 2 nitrogen atoms, and are optionally substituted with one or more of alkyl, aryl, amine, C(O), C(O)R, S, S(R), O, O(R), amide, $SR_4$, $PR_4$, $OR_4$, halogen, $SO_3H$, alkylamino and P, wherein R is selected from H, OH, alkyl, and aryl; or a pharmaceutically acceptable derivative thereof; and exposing a site of the subject to light after the step of administering the compound.

22. The method of claim 21, wherein, in the exposing step, the compound releases one or more of $X_1$, $X_2$, and $X_3$.

23. The method of claim 21, wherein at least one of $X_1$, $X_2$, and $X_3$ are polypyridyl.

24. The method of claim 21, wherein at least one of $X_1$, $X_2$, and $X_3$ are selected from:

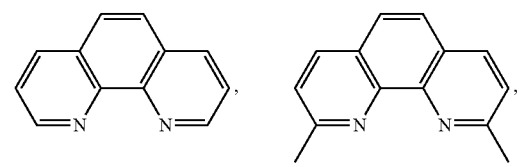

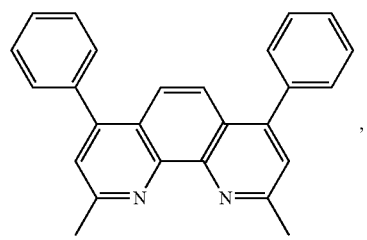

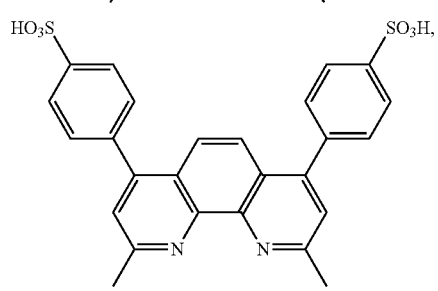

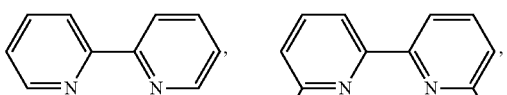

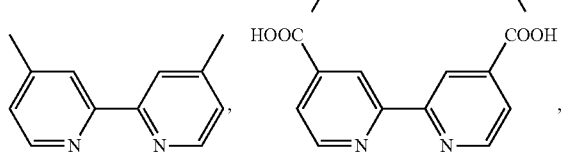

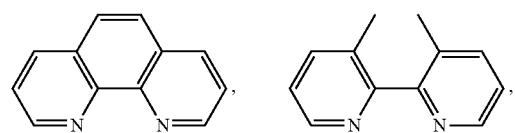

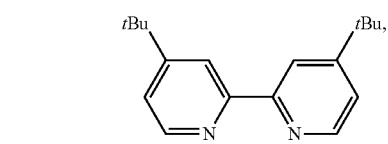

-continued

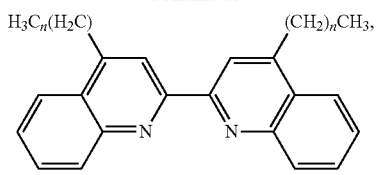

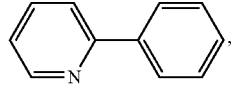

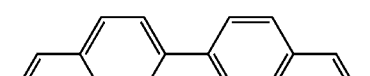

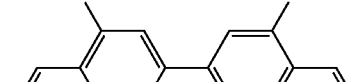

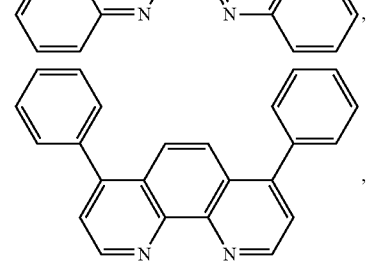

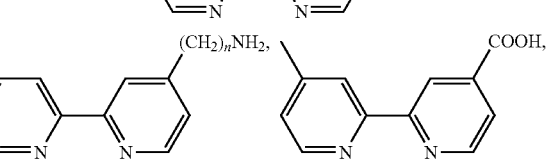

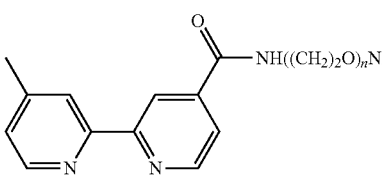

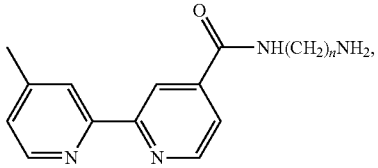

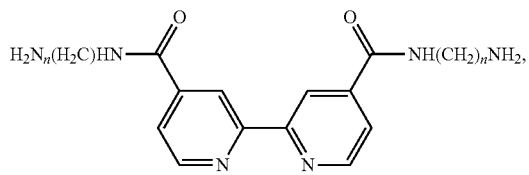

-continued
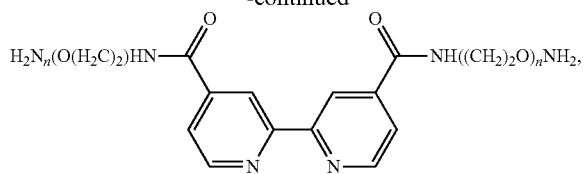
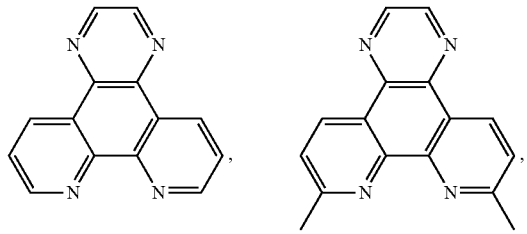
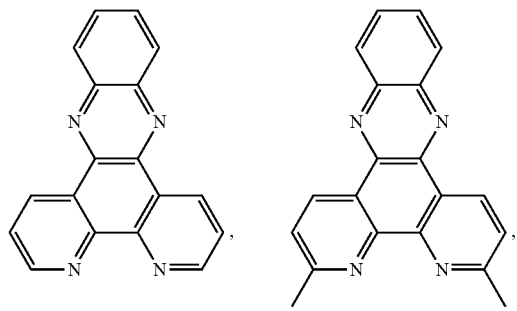
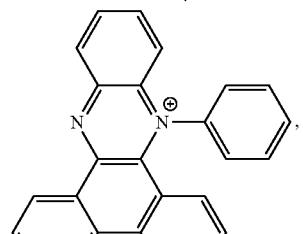
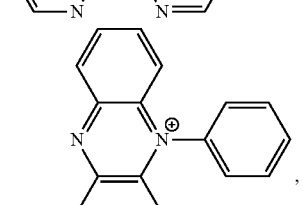
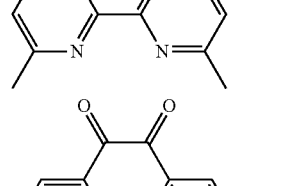
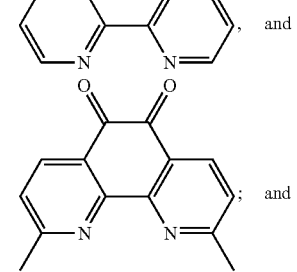
wherein when the at least one of $X_1$, $X_2$, and $X_3$ is
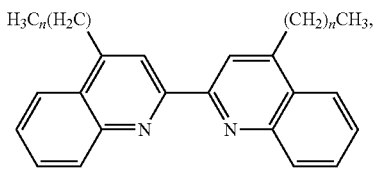
n is from 1 to 16,
when the at least one of $X_1$, $X_2$, and $X_3$ is
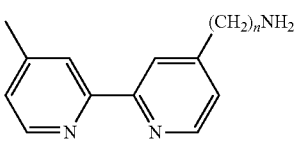
n is 5, 7, or 9;
when the at least one of $X_1$, $X_2$, and $X_3$ is
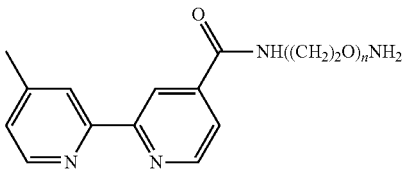
n is 2 or 4;
when the at least one of $X_1$, $X_2$, and $X_3$ is
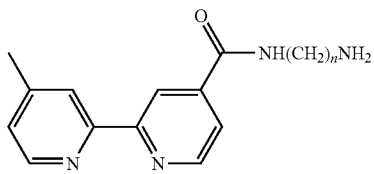
n is 4 or 8;
when the at least one of $X_1$, $X_2$, and $X_3$ is
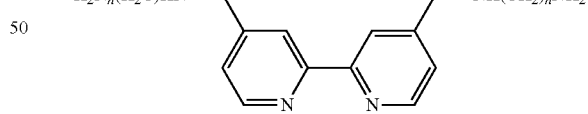
n is 4 or 8; and
when the at least one of $X_1$, $X_2$, and $X_3$ is
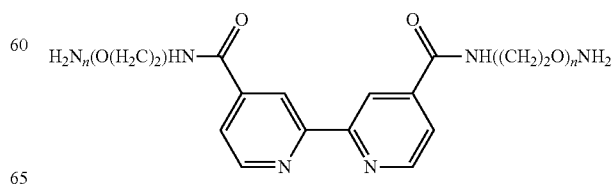
n is 2 or 4.

25. The method of claim 21, wherein at least one of $X_1$, $X_2$, and $X_3$ are a methylated bidentate nitrogen heterocycle.

26. The method of claim 21, wherein the compound further comprises a targeting agent.

27. The method of claim 26, wherein the targeting agent selected from folate, estrogen, and erlotinib.

28. The method of claim 21, wherein at least one of the ligands is a therapeutic agent.

29. The method of claim 28, wherein the therapeutic agent is hydroxyquinoline.

30. The method of claim 21, wherein the light includes a wavelength of about 350 nm to about 1000 nm.

31. The method of claim 21, wherein the light includes a wavelength of about 500 nm to about 1000 nm.

32. The method of claim 21, wherein m is less than zero.

33. The method of claim 21, wherein the site is a tumor or in proximity to a tumor.

34. The method of claim 21, wherein the step of administering includes administering the compound by oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, subcutaneous administration, or combinations thereof.

\* \* \* \* \*